United States Patent [19]

Rzeszotarski et al.

[11] Patent Number: 4,889,860

[45] Date of Patent: * Dec. 26, 1989

[54] OXIMES OF OXYMORPHONE, NALTREXONE AND NALOXONE AS POTENT, SELECTIVE OPIOID RECEPTOR AGONISTS AND ANTAGONISTS

[75] Inventors: Waclaw J. Rzeszotarski, Millersville; Babu J. Mavunkel, Baltimore, both of Md.

[73] Assignee: Nova Pharmaceutical Corporation, Baltimore, Md.

[ * ] Notice: The portion of the term of this patent subsequent to Jul. 26, 2005 has been disclaimed.

[21] Appl. No.: 35,034

[22] Filed: Apr. 6, 1987

Related U.S. Application Data

[63] Continuation-in-part of Ser. No. 778,800, Sep. 23, 1985, Pat. No. 4,760,069.

[51] Int. Cl.$^4$ .................. A61K 31/485; C07D 489/08
[52] U.S. Cl. ........................................ 514/282; 546/45
[58] Field of Search ........................... 544/45; 514/282

[56] References Cited

U.S. PATENT DOCUMENTS 3,135,758  6/1964  Fishman ................................ 546/45
3,153,042 10/1964  Fishman ................................ 546/45
3,320,262  5/1967  Lewenstein et al. ................. 546/45

OTHER PUBLICATIONS

Baskin, D. S., Y. Hosobuchi, H. H. Loh and N. M. Lee, Dynorphin$_{1-13}$ Improves Survival in Cats with Focal Cerebral Ischemia. *Nature*, 312: 551–552, 1984.

Kuroda, H., D. S. Baskin, T. Matsui, H. H. Loh, Y. Hosobuchi and N. M. Lee, Effects of Dynorphin$_{1-13}$ on Opiate Binding and Dopamine and GABA Uptake in Stroked Cat Brain. *Brain Res.*, 379: 68–74, 1986.

Silvia and Tang. Protection of Ischemia—Induced Cerebral Edema by the Kappa Opioid Agonist U—50488, In: Pharmacology of Cerebral Ischemia, edt by J. Krieglstein, Elsevier, 1986. pp. 381–384.

Silvia, Slizgi, Ludens and Tang. Protection from Ischemia—Induced Cerebral Edema in the Rat by U–50488H, a Kappa Opioid Receptor Agonist. *Brain Res.*, 403: 52–57, 1987.

Lason, Simpson and McGinty. The Effects of the Kappa Opioid Receptor Agonist U50488H on Kainic Acid Neurotoxicity. *Soc. Neurosci. Abstr.* 13:1306, 1987.

Tang, Protection from Cerebral Ischemia by U50,488E, A Specific Kappa Opioid Analgesic Agent, *Life Sci.*, 37: 1475–1482, 1985.

Ochoa, Jackson, Aaron and VonVoigtlander, Mechanism of Anticonvulsant and Cerebroprotective Activity of U–50488H and U–54494A. *Soc. Neurosci. Abstr.* 13: 765, 1987.

VonVoigtlander, Hall, Ochoa, Lewis and Triezenberg, U–54494A: A Unique Anticonvulsant Related to Kappa Opioid Agonists. *J. Pharmacol. Exp. Ther.* 234: 542–547, 1987.

(List continued on next page.)

Primary Examiner—Mukund J. Shah, PhD
Assistant Examiner—Diana G. Rivers
Attorney, Agent, or Firm—Breneman & Georges

[57] ABSTRACT

A potent, selective opioid receptor agonist or antagonist exhibiting properties useful for a longacting analgesic or opiate abuse treatment agent or appetite suppressant having the general formula:

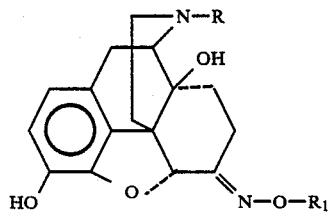

wherein R is methyl, cyclopropylmethyl or allyl, and $R_1$ is an unsubstituted or substituted aryl, aralkyl, heteroaryl, heteroaralkyl or a cycloalkyl group with or without a heteroatom like S,O,N; and the pharmaceutically acceptable salts thereof.

22 Claims, 15 Drawing Sheets

OTHER PUBLICATIONS

Tortella, Robles and Holaday, U50,488, A Highly Selective Kappa Opioid: Anticonvulsant Profile in Rats, J. Pharmacol. Exp. Ther. 237: 49–53, 1986.

Moises and Walker, Electrophysiological Effects of Dynorphin Peptides on Hippocampald Pyramidal cells in rat, Eur. J. Pharmaco; Bradley and Brooks, A Microiontophoretic Study of the Actions of 1th, 2 and K-Opiate Receptor Agonists in the Rat Brain. Br. J. Pharmac. 83:763–772, 1984.

Bernton, Long and Holaday, Opioids and Neuropeptides: Mechanisms in Circulatory Shock, Fedn. Proc. 44: 290–299, 1985.

Holaday, Cardiovascular Consequences of Endogenous Opiate Antagonism, *Biochem. Pharmacol.* 32: 573–585, 1983.

Feuerstein, The Opioid System and Central Cardiovascular Control: Analysis of Controversies, Peptides 6 (Suppl. 2): 51–56, 1985.

D'Amato and Holaday, Multiple Opioid Receptors in Endotoxic Shock: Evidence For Delta Involvement and Mu—Delta Interactions in Vivo. Proc. Natl. Acad. *Sci. USA,* 81: 2898–2901, 1984.

Long, Ruvio, Glatt and Holaday, ICI 174,864, A Putative Delta Opioid Antagonist, Reverses Endotoxemic Hypotension: Pretreatment with Dynorphin$_{1-13}$, A K Agonistblocks This Action. *Neuropeptides* 5: 291–294, 1984.

McKenzie, Anselmo and Muldoon, Nalbuphine's Reversal of Hypovolemic Shock in the Anesthetized Rat. Circ. Shock 17: 21–33, 1985.

Paciorek, Todd and Waterfall, The Effects of Meptazinol in Comparison with Pentazocine, Morphone and Nalozone in a Rat Model of Anaphylactic Shock, *Br. J. Pharmacol.* 84:469–475, 1985.

Shavit, Terman, Martin, Lewis, Liebeskind an Gale, Stress, Opioid Peptides, the Immune System and Cancer. J. *Immunol.* 135: 834s–837s, 1985.

Teschemacher and Schweigerer, Opioid Peptides: Do they have Immunological Significance? Trends Pharmacol. Sci. 6: 368–370, 1985.

Holaday, Endogenous Opioids and Their Receptors, *Current Concepts.* Kalamazoo, MI, Scope Publications, Upjohm, 1985.

Shavit, Depaulis, Martin, Terman, Pechnick, Zane, Gale and Liebeskind, Involvement of Brain Opiate Receptors in the Immune—Suppressive Effect of Morphine. *Proc. Natl. Acad. Sci. USA,* 83: 7114–7117, 1986.

Shavit, Lewis, Terman, Gale and Liebeskind, Opioid Peptides Mediate the Suppressive Effect of Stress on Natural Killer Cell Cytoxicity, Science, 223, 188–190, 1984.

Rapoport, et al., J. Organic Chem., vol. 15, pp. 1103–06, (1950).

Bentley, "The Chemistry of the Morphine Alkaloids", Oxford (1954), pp. 180, 259.

Sawa et al., Tetrahedron, vol. 24, pp. 6185–6196, (1968).

Hahn, et al., J. Pharm. & Pharmacology, vol. 35(17), pp. 833–36, (12/83).

Ko, et al., J. Med. Chem., vol. 27(12), pp. 1727–1729, (12/84).

Koolpe, et al., J. Med. Chem., vol. 28(7), pp. 949–957, (07/85).

Mohamed, et al., Chemical Abstracts, vol. 104, 88886t, (196).

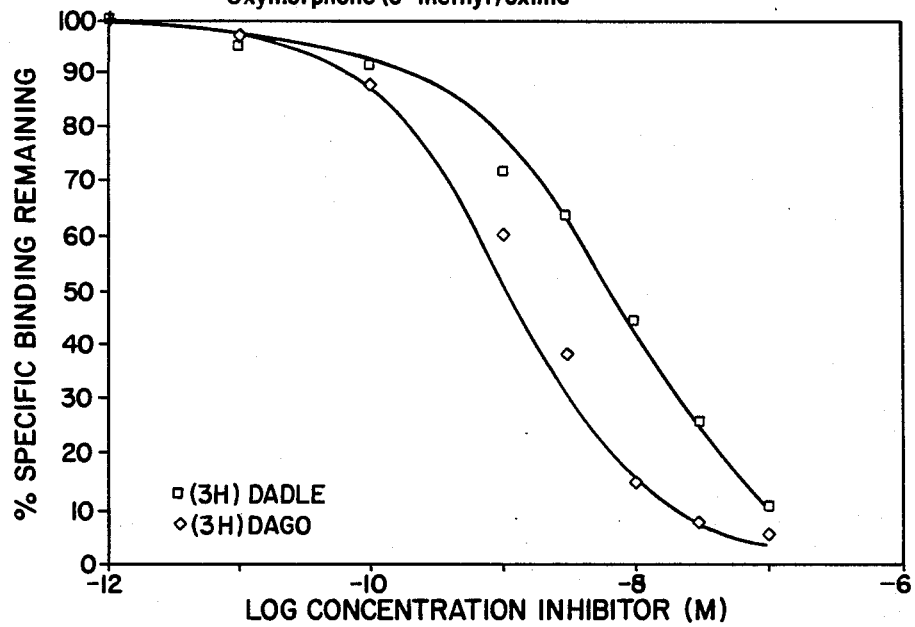
Fig.1 COMPOUND II vs (3H) OPIATES Oxymorphone (o-methyl)oxime
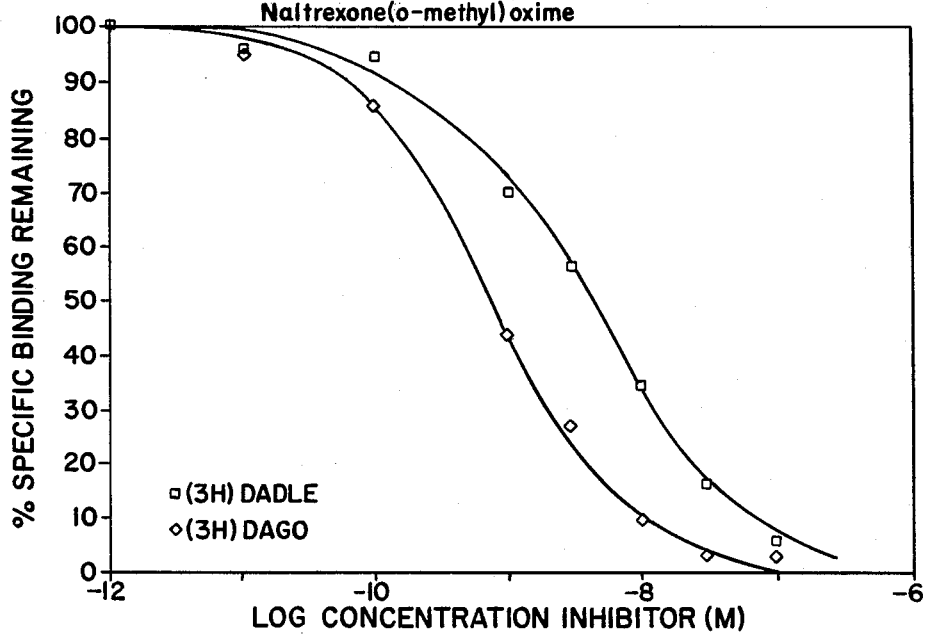
Fig.2 COMPOUND X vs (3H) OPIATES Naltrexone(o-methyl)oxime COMPOUND IV vs (3H) OPIATES
Oxymorphone (o-phenyl)oxime COMPOUND XII vs (3H) OPIATES
Naltrexone (o-phenyl)oxime

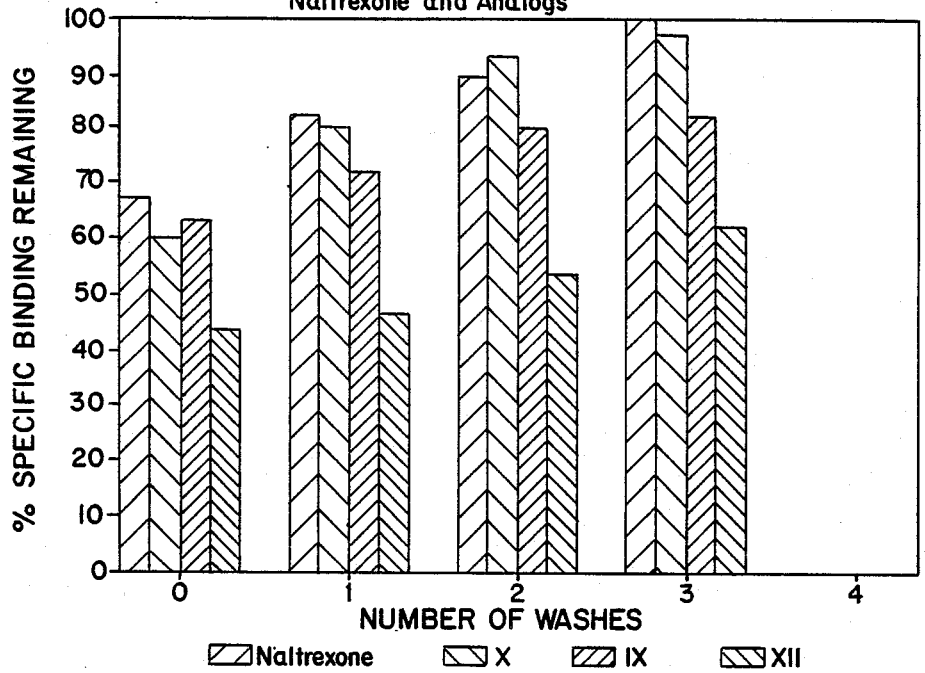
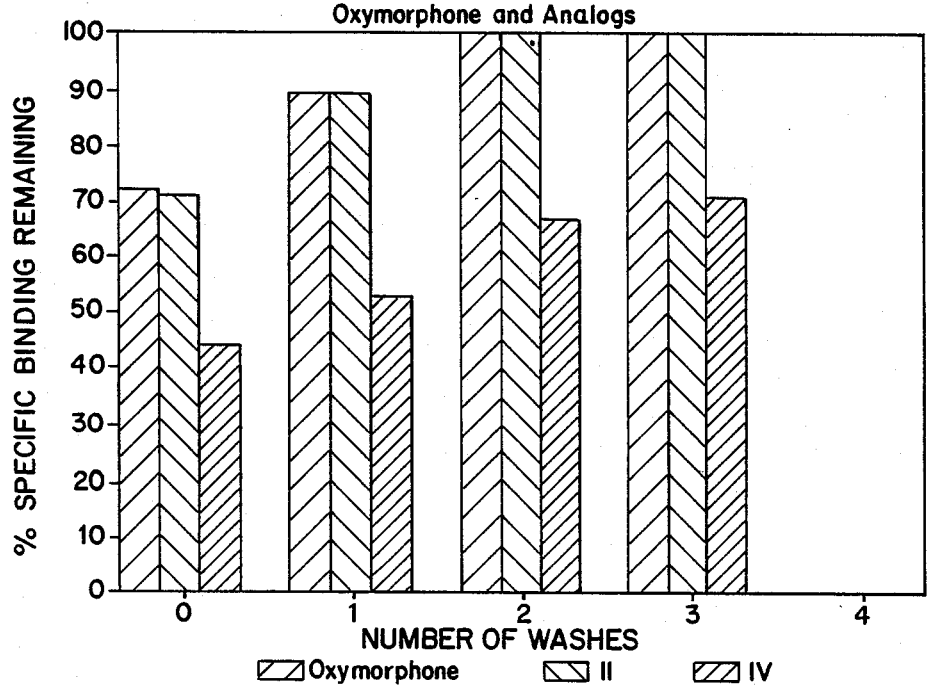

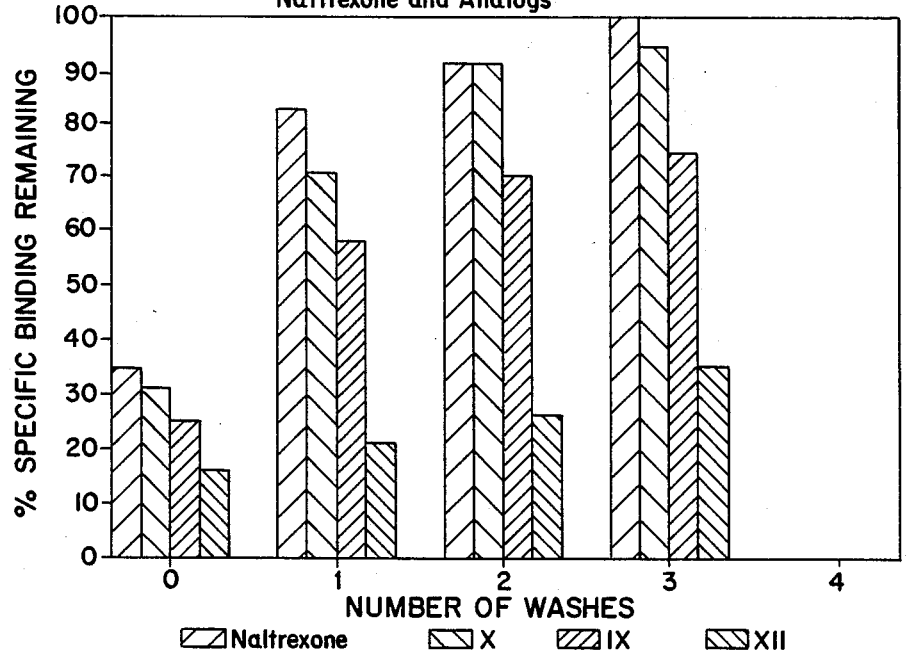
Fig.9 REVERSIBILITY OF (3H)DAGO BINDING — Naltrexone and Analogs
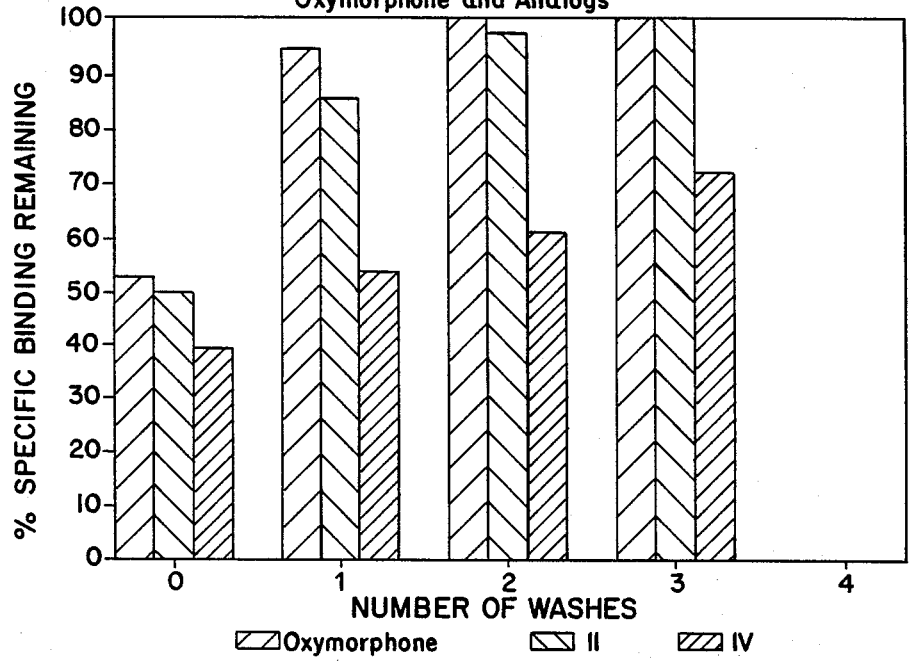
Fig.10 REVERSIBILITY OF (3H)DAGO BINDING — Oxymorphone and Analogs

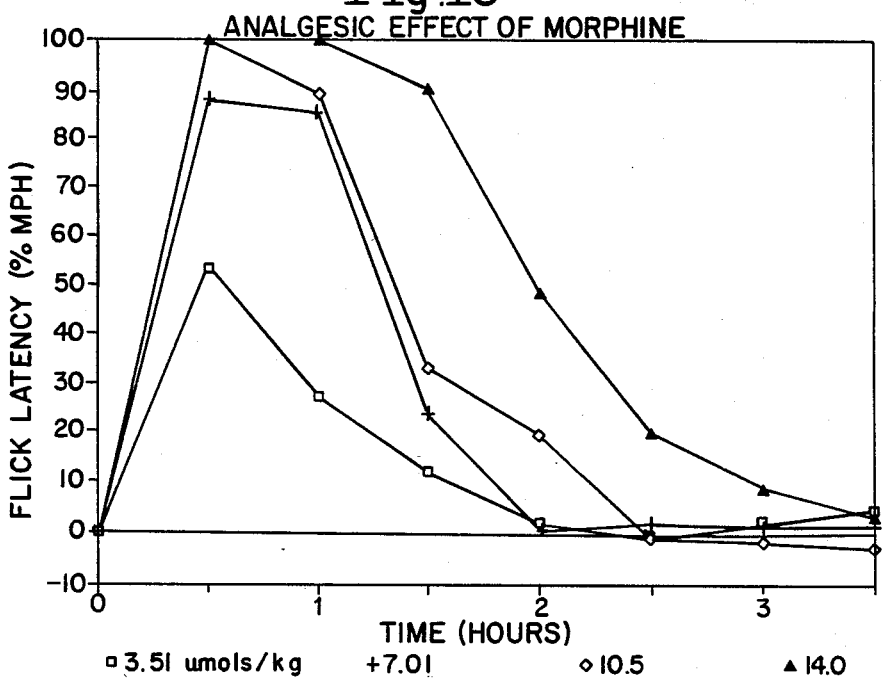
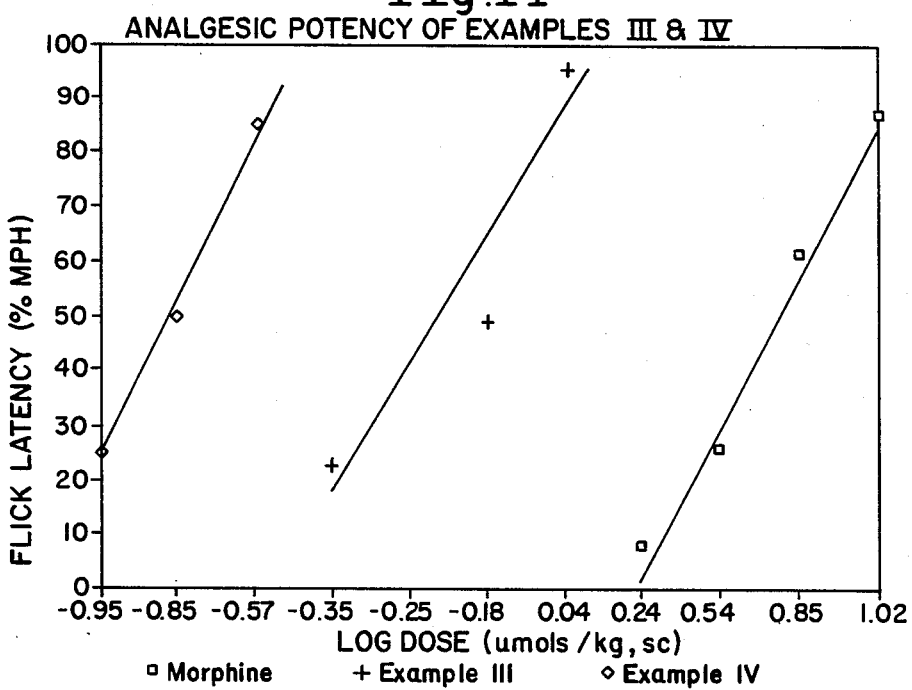

OXIMES OF OXYMORPHONE, NALTREXONE AND NALOXONE AS POTENT, SELECTIVE OPIOID RECEPTOR AGONISTS AND ANTAGONISTS

This application is a continuation-in-part of Ser. No. 778,800, filed 9/23/85, now U.S. Pat. No. 4,760,069.

BACKGROUND OF THE INVENTION

1. Field of the Invention

The present invention pertains to novel long-acting analgesics, prophylactic or rescue agents in the treatment of opiate drug abuse and a new class of antiobesity drugs. In particular, the invention is directed to O-aryl or O-aralkyl ethers of oxymorphone, naltrexone and naloxone derived oximes, their pharmaceutically acceptable salts and to the methods of synthesizing the same.

2. Description of the Prior Art

The evidence for multiplicity of opioid receptor subtypes in the prior art lead to the discovery of novel selective agonists and antagonists as reported in Lever et al. *Ann. Rep. Med. Chem.*, 18, 51 (1983). The discovery of a potent, selective agonist or antagonist reduces or eliminates the side effects associated with a nonselective compound. Increased potency and selectivity of the agonist and antagonist compounds generally results in a reduction of overall toxicity since less compound is generally required. Thus, in the case of analgesics, morphine and related opiates exhibit deleterious side effects such as respiratory depression, mood changes, and decreased intestinal motility with concomitant constipation, nausea, vomiting and alterations in the endocrine and autonomic nervous systems. Opiate antagonists in the prior art have been reported to show as side effects endocrine and gastrointestinal disturbance. The novel compounds of the present invention are improved over prior art opiate compounds in potency and selectivity as opioid receptor agonists and antagonists and in reducing or being substantially free of reported side effects of prior art opiate compounds.

Some of the prior art compounds which have been associated with mu or delta agonist activity have demonstrated analgesic activity. The primary drawback with these prior art compounds when used as opioid analgesics is the respiratory depression as documented in Holiday, J. W. *Current Concepts* Scope Publications, Upjohn, Kalamazoo, Mi., 1985. On the other hand, opioid agonists prepared by Von Voigtlander, Journal of Pharmacol. Exp. Therap. 224: 7-12, 1983, have been shown to be selective to kappa - type opioid receptors which are suitable as analgesics with the advantage that they do not produce respiratory depression at analgesic doses.

Considerable evidence from radioligand binding studies in the prior art supports the existence of mu, delta, kappa and sigma opioid receptors [Simone et al. and in *Opioids-Past, Present and Future*, Tylor and Francis, London, pp 33–52, (1984) and Martin et al. *J. Pharmacol. Exp. Therap.* 196, 66 (1976)]. The mu-receptor was originally believed to be involved in the production of both analgesic and respiratory depressant effects. A more recent study suggests that one subclass of that receptor ($mu_1$) is responsible for the former and the other ($mu_2$) for the latter [Spiegel et al. *J. Pharmacol. Exp. Therap.* 228, 414 (1984)]. Subsequently the original group of investigators (Simone et al. *Life Sci.* in press (1985)) reported inhibition of overnight feeding by a $mu_1$-selective antagonist, naloxonazine.

The novel compounds of the present invention were the product of an extensive research investigation into the possible relationship between the hydrophobic bonding region present in the vicinity of the C-6 position of the opiate molecule when bound to the mu-receptor. The existence of the hydrophobic bonding region was clearly demonstrated by Pasternak et al. *J. Med. Chem.* 23, 674 (1980) in studies using the dimeric azines and the phenyl-hydrazones (Hahn et al. *J. Pharmacol. Exp. Therap.* in press (1985)). The ease of formation of oximes in the 14-hydroxy dihydromorphinone series has been the subject of a number of prior art references the most pertinent of which are believed to be Lewenstein et al. U.S. Pat. No. 3,320,262; Sawa et al. *Tetrahedron*, 24, 6185 (1968); Ko et al. *J. Med. Chem.* 27, 1727 (1984). The two known groups of oximes tested in the past were esters of carboxymethyl oximes [Lowenstein et al. U.S. Pat. No. 3,320,262] and oximes and their O-methyl ethers of oxymorphone, naloxone and naltrexone [Ko et al. *J. Med. Chem.* 27, 1727, (1984)].

In U.S. Pat. No. 3,320,262 only one compound, N-cyclopropylmethyl-nor-14-hydroxydihydrocodeinone-6-carboxymethyl methyl ester was examined in morphine dependent monkeys. At dosages of 1 and 2 mg/kg of body weight only, "partial suppression of symptoms was obtained" (Col. 6, ls. 67–71 of the patent). In the Ko et al. study the oximes and their O-methyl ethers of oxymorphone, naloxone and naltrexone were reported as less potent than parent ketones.

The unusually high potency and selectivity exhibited by the novel compounds of the invention is not disclosed or suggested in the available prior art. The novel and unexpected advantages of the potent selective opioid receptor agonists and antagonists over the prior art are further illustrated in the accompanying drawings together with the summary of the invention.

SUMMARY OF THE INVENTION

The present invention provides a potent, selective opioid receptor agonist or antagonist having the general formula:

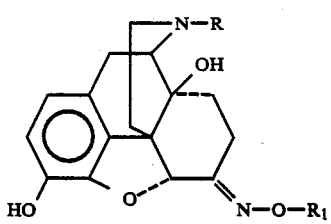

wherein R is cyclopropylmethyl, allyl or methyl, and $R_1$ is an unsubstituted or substituted aryl, aralkyl, heteroaryl, heteroaralkyl or a cycloalkyl group, with or without a heteroatom like S,O,N; and the pharmaceutically acceptable salts thereof.

DESCRIPTION OF THE DRAWINGS

Other advantages of the invention will become apparent to those skilled in the art from the following detailed description of the invention in conjunction with the accompanying drawings in which:

FIG. 1 is a graph illustrating representative inhibition of specific [$^3$H]DAGO ([$^3$H]-[D-Ala$^2$-MePhe$^4$-Gly-ol$^5$]-enkephalin) or [$^3$H]DADLE ([$^3$H]-[D-Ala$^2$-D-Leu$^5$]-enkephalin) binding to rat brain membranes of 6-

Figure 3:
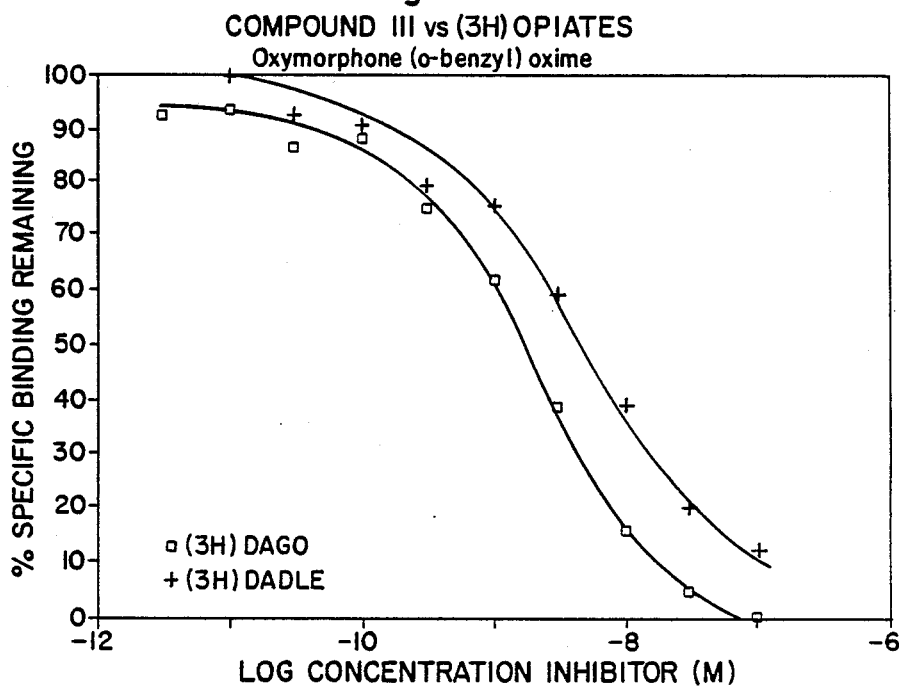
Figure 4:
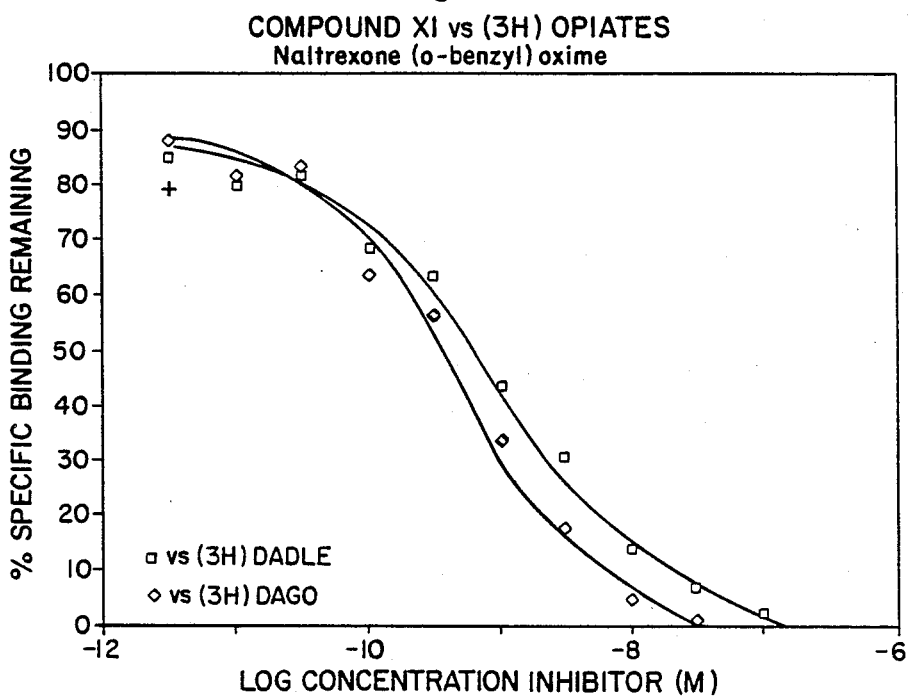
Figure 5:
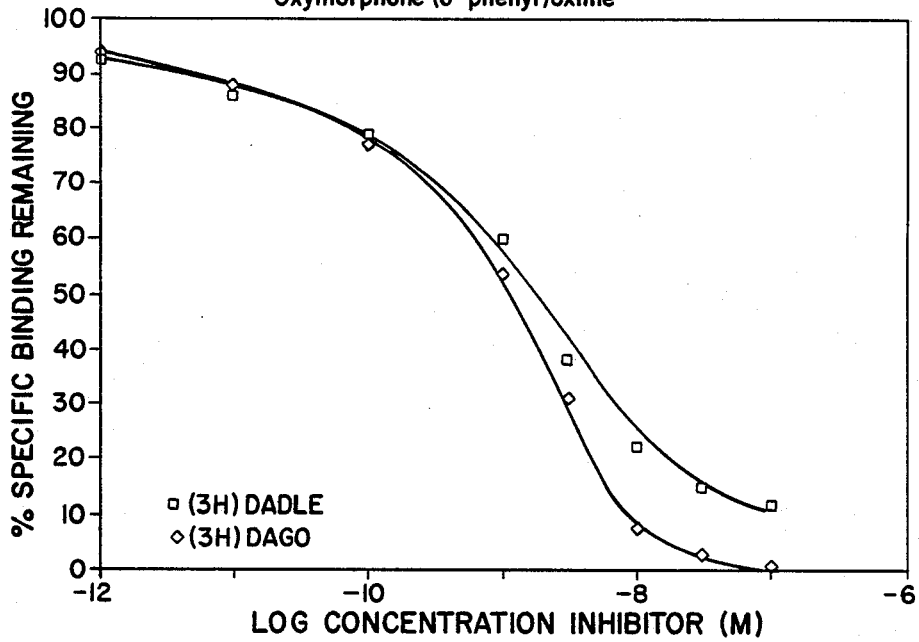
Figure 6:
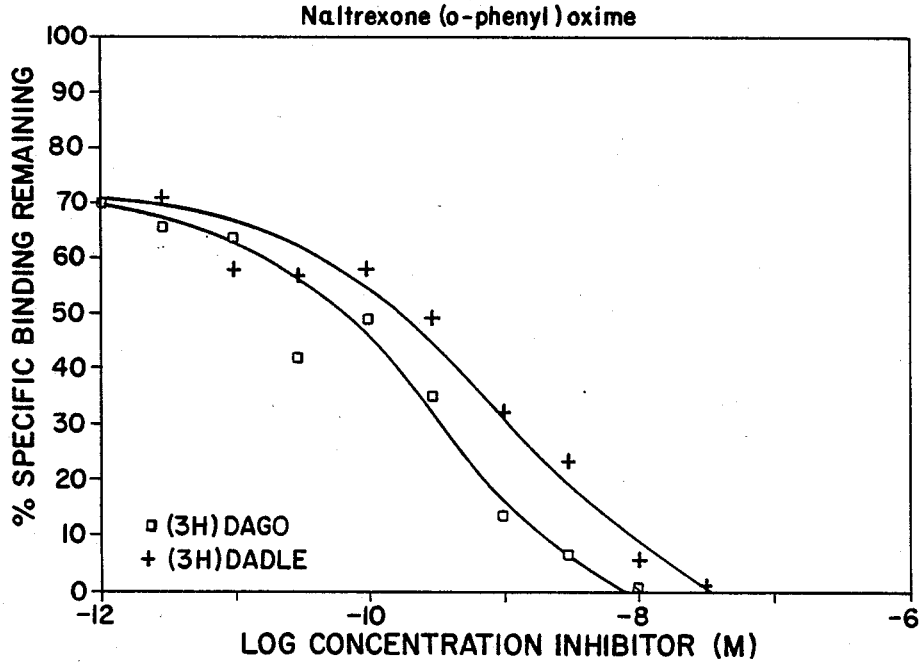
Figure 11:
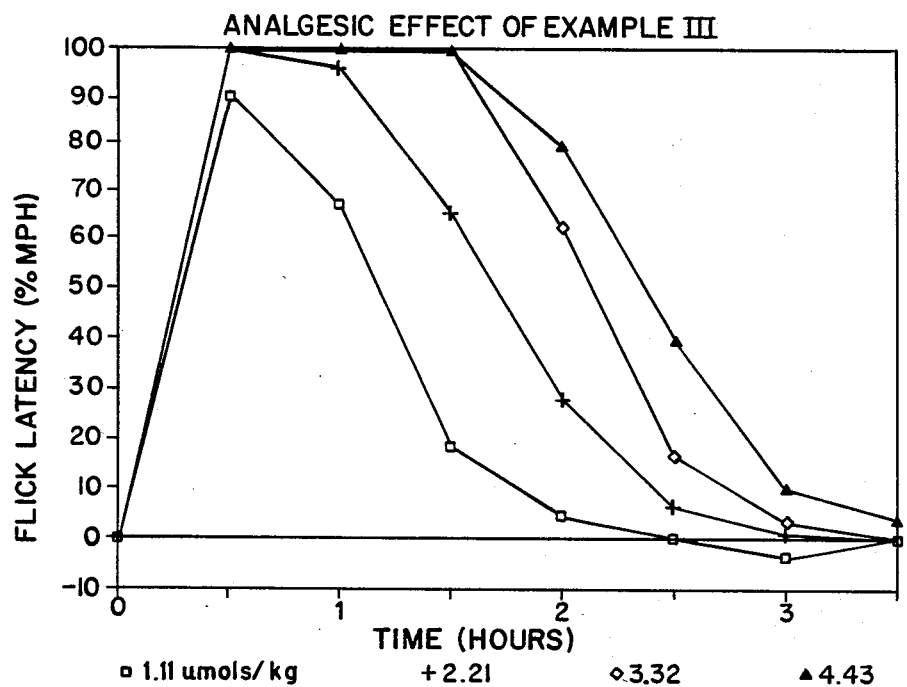
Figure 12:
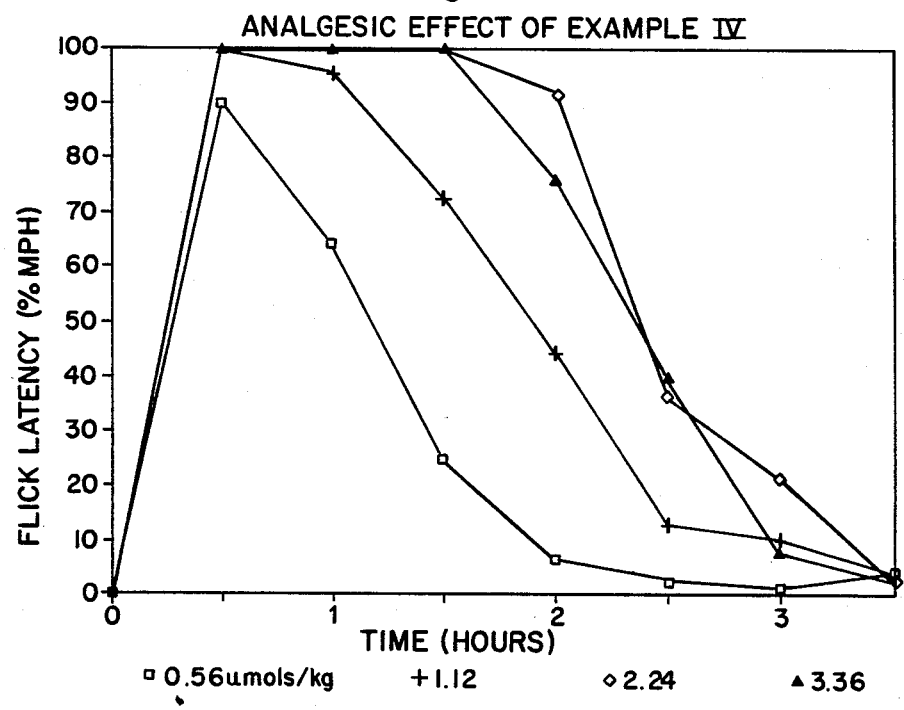
Figure 15:
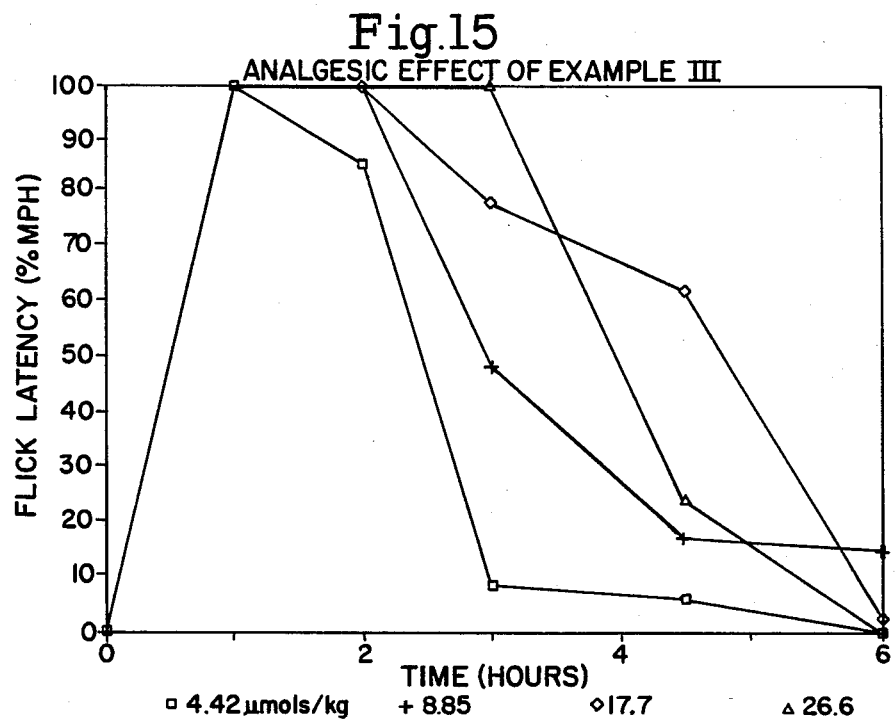
Figure 16:
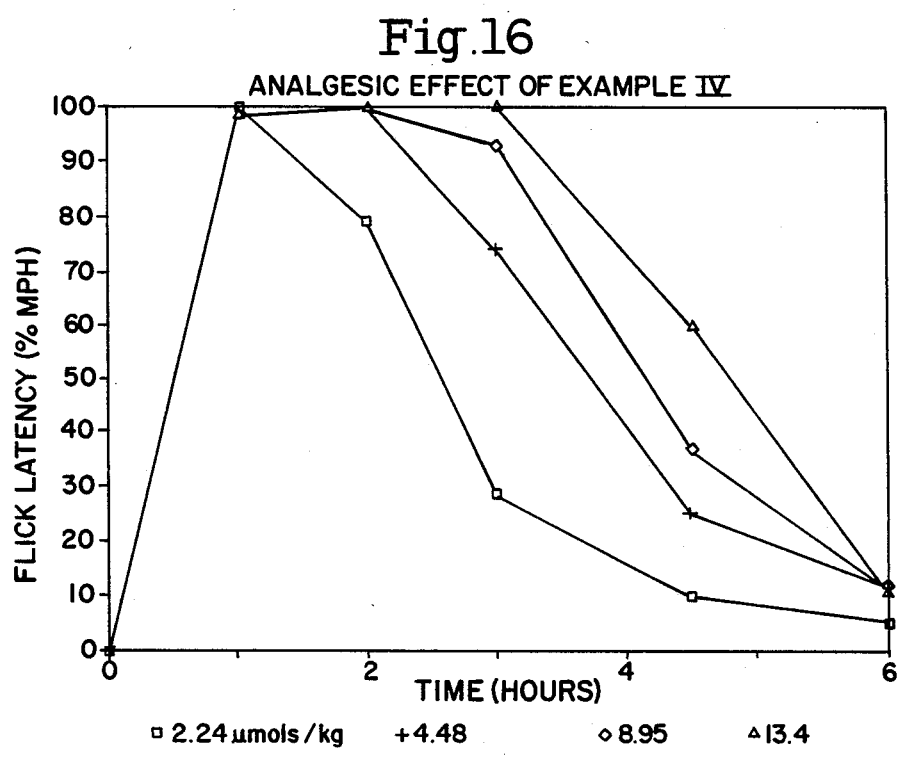
Figure 18:
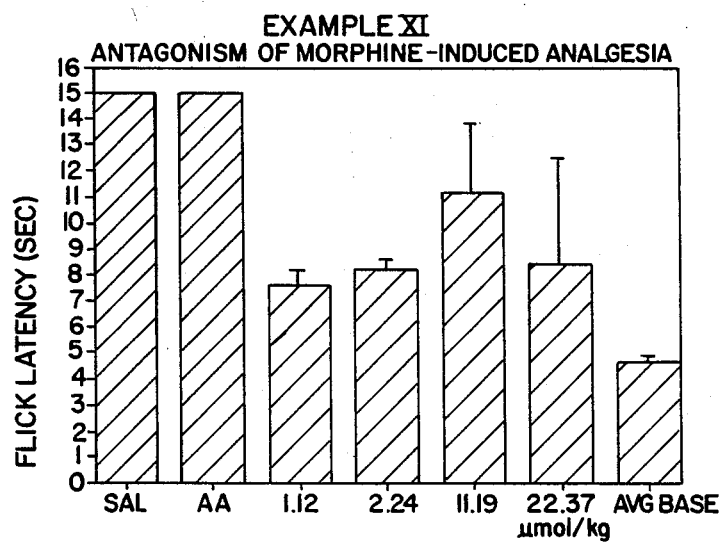
Figure 19:
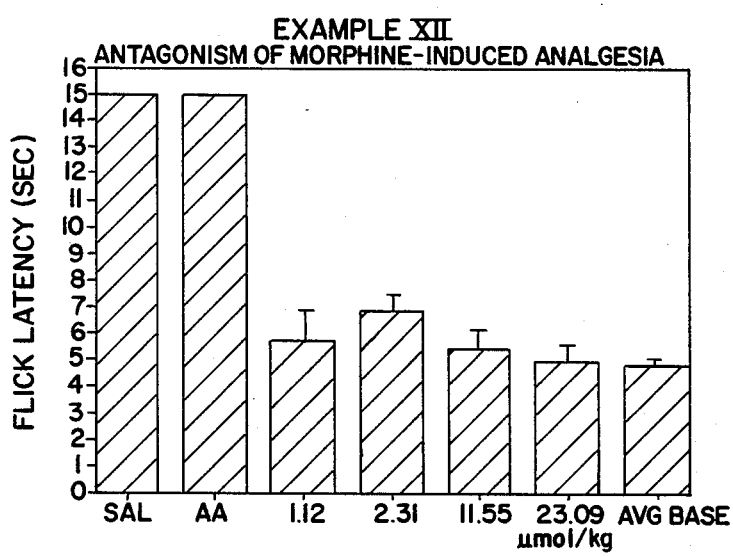
Figure 21:
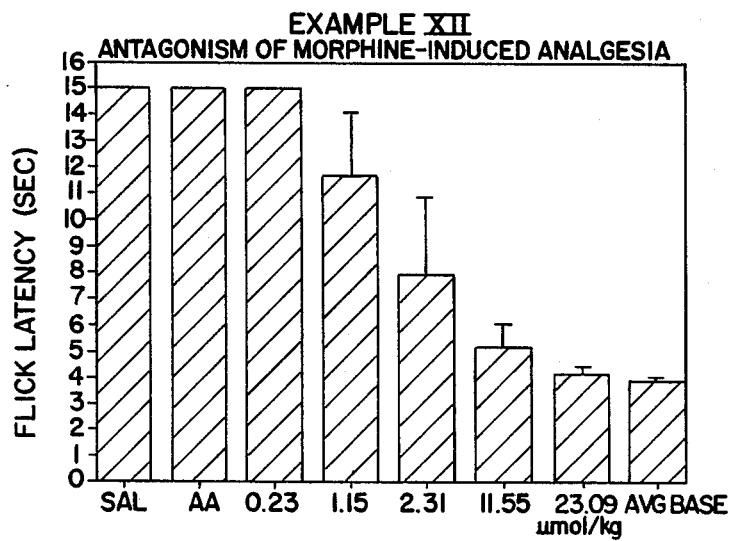
Figure 23:
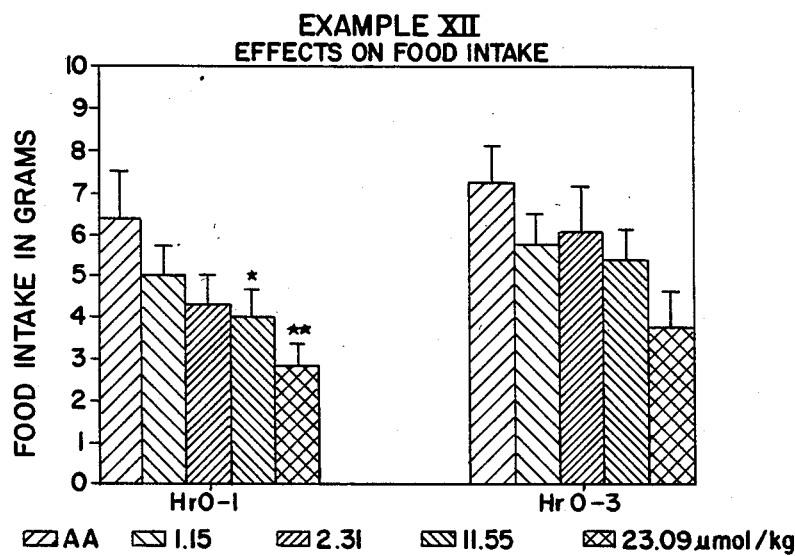
Figure 25:
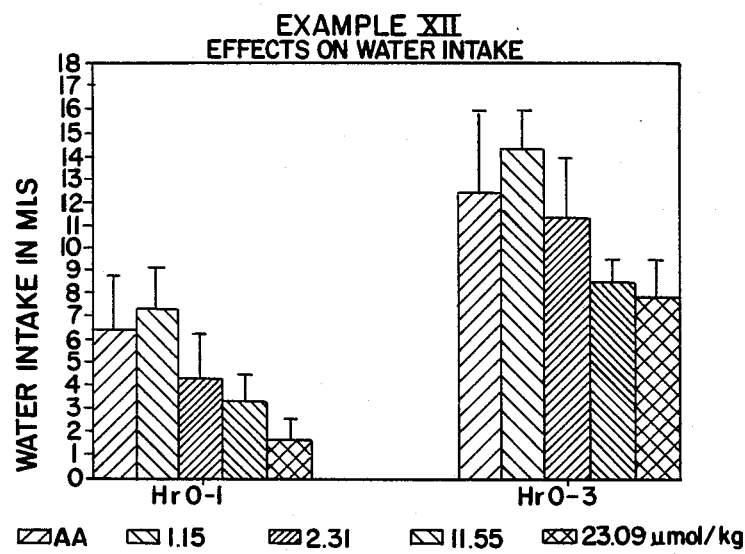
Figure 27:
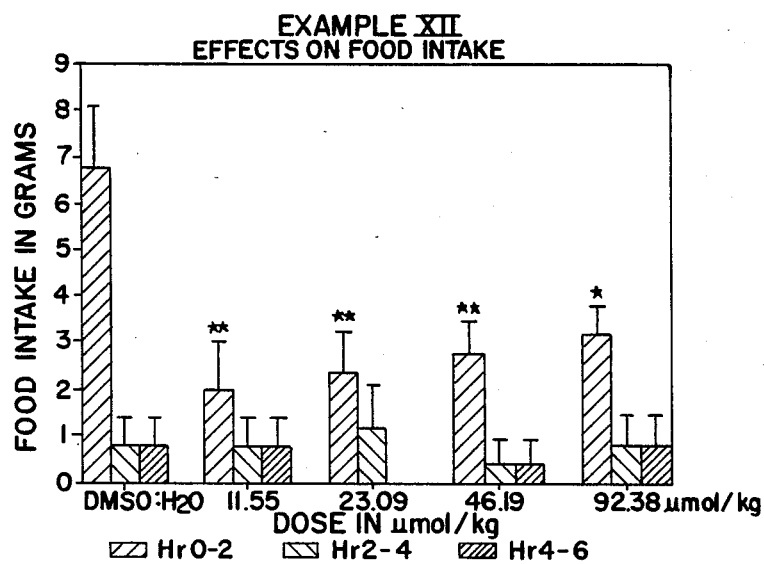
Figure 28:
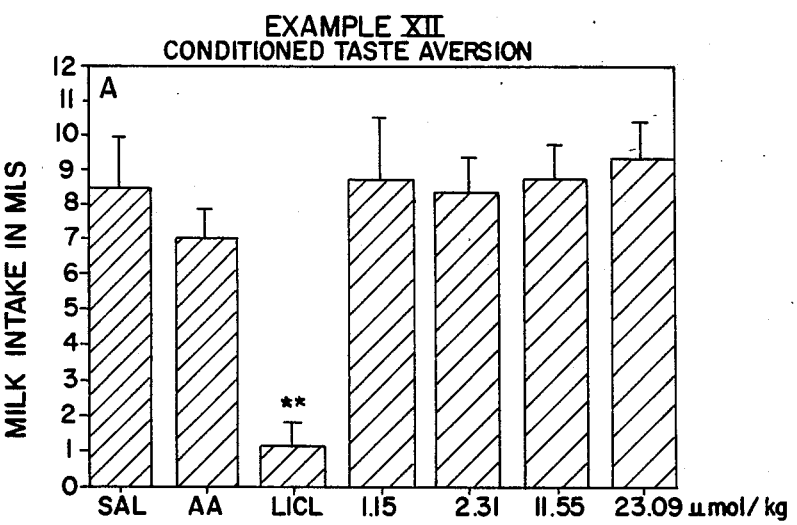
Figure 29:
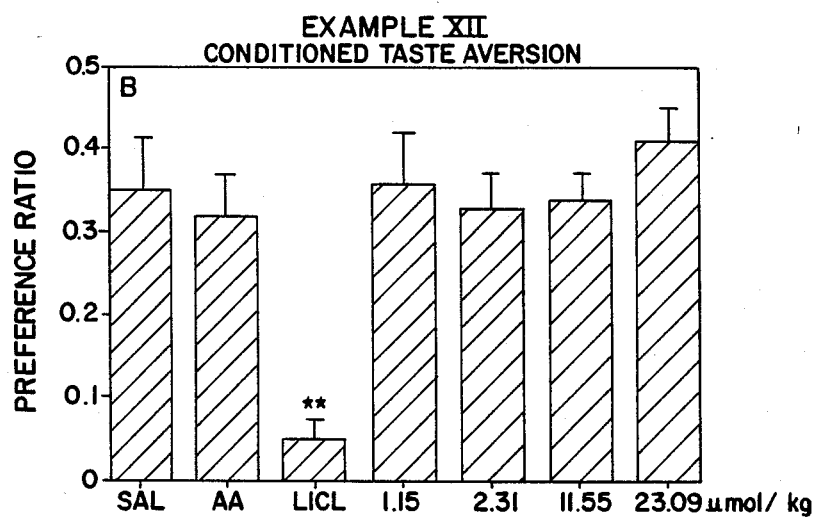
Figure 31:
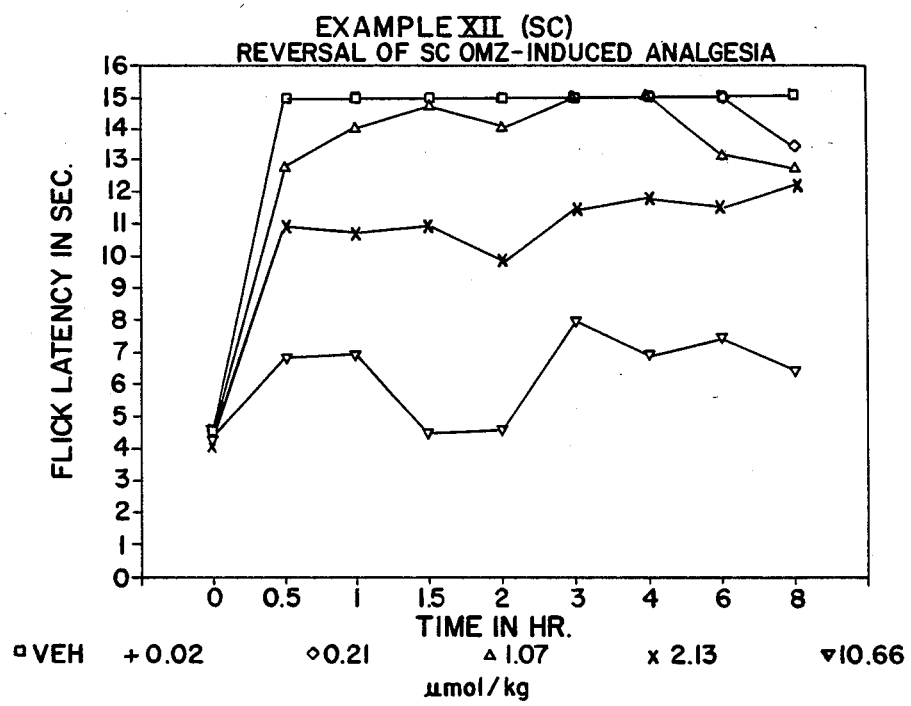
Figure 33:
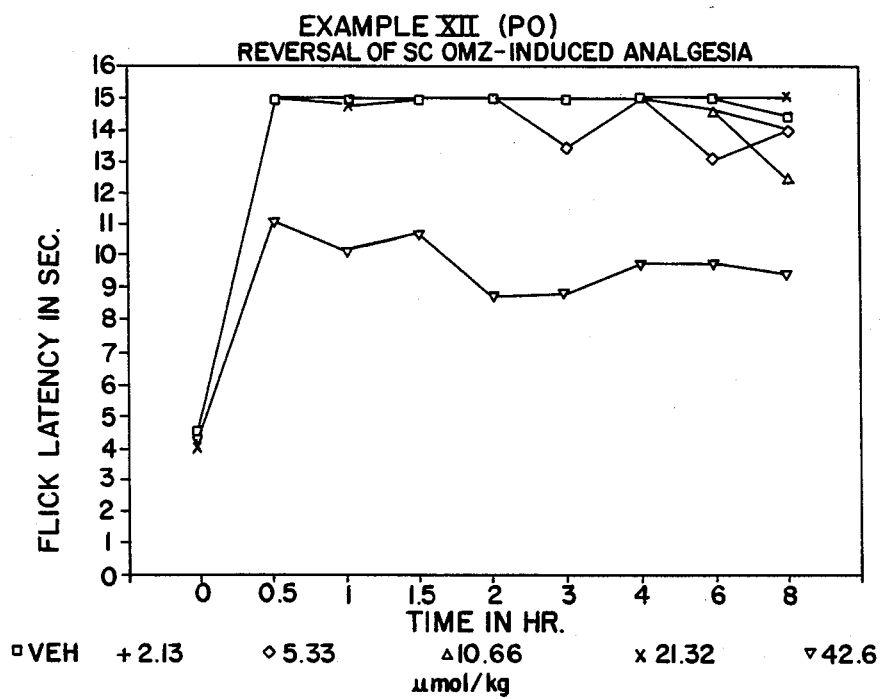

Methyloximino-17-methyl-4,5 α-epoxy-3, 14-dihydroxymorphinan (compound II of Example II);

FIG. 2 is a graph illustrating representative inhibition of specific [$^3$H]DAGO or [$^3$H]DADLE binding to rat brain membranes of 6-Methyloximino-17-cyclopropylmethyl-4,5 α-epoxy-3, 14-dihydroxymorphinan (compound X of Example X);

FIG. 3 is a graph illustrating representative inhibition of specific [$^3$H]DAGO or [$^3$H]DADLE binding to rat brain membranes of 6-Benzyloximino-17-methyl-4,5 α-epoxy-3, 14-dihydroxymorphinan (compound III of Example III);

FIG. 4 is a graph illustrating representative inhibition of specific [$^3$H]DAGO or [$^3$H]DADLE binding to rat brain membranes of 6-Benzyloximino-17-cyclopropylmethyl-4, 5 α-epoxy-3, 14-dihydroxymorphinan (compound XI of Example XI);

FIG. 5 is a graph illustrating representative inhibition of specific [$^3$H]DAGO or [$^3$H]DADLE binding to rat brain membranes of 6-Phenyloximino-17-methyl-4,5 α-epoxy-3, 14-dihydroxymorphinan (compound IV or Example IV);

FIG. 6 is a graph illustrating representative inhibition of specific [$^3$H]DAGO or [$^3$H]DADLE binding to rat brain membranes of 6-Phenyloximino-17-cyclopropylmethyl-4,5 α-epoxy-3, 14-dihydroxymorphinan (compound XII of Example XII);

FIG. 7 is a graph illustrating the reversibility of inhibition of [$^3$H]DADLE binding as a result of pretreatment of rat forebrain membranes with naltrexone, 6-Methyloximino-17-cyclopropylmethyl-4,5 α-epoxy-3, 14-dihydroxymorphinan (compound X of Example X), 6-Oximino-17-cyclopropylmethyl-4,5 α-epoxy-3, 14-dihydroxymorphinan (compound IX of Example IX) and 6-Phenyloximino-17cyclopropylmethyl-4,5 α-epoxy-3, 14-dihydroxymorphinan (compound XII of Example XII);

FIG. 8 is a graph illustrating the reversibility of inhibition of [$^3$H]DADLE binding as a result of pretreatment of rat forebrain membranes with oxymorphone, 6-Methyloximino-17-methyl-4,5 α-epoxy-3, 14-dihydroxymorphinan (compound II of Example II), and 6-Phenyloximino-17-methyl 4,5 α-epoxy-3, 14-dihydroxymorphinan (compound IV of Example IV);

FIG. 9 is a graph illustrating the reversibility of inhibition of [$^3$H]DAGO binding as a result of pretreatment of rat forebrain membranes with naltrexone, 6-Methyloximino-17-cyclopropylmethyl-4,5 α-epoxy-3, 14-dihydroxymorphinan (compound X of Example X), 6-Oximino-17-cyclopropylmethyl-4,5 α-epoxy-3, 14-dihydroxymorphinan (compound IX of Example IX) and 6-Phenyloximino-17 cyclopropylmethyl -4,5 α-epoxy-3, 14-dihydroxymorphinan (compound XII of Example XII);

FIG. 10 is a graph illustrating the reversibility of inhibition of [$^3$H]DAGO binding as a result of pretreatment of rat forebrain membranes with oxymorphone, 6-Methyloximino-17-methyl-4,5α-epoxy-3, 14-dihydroxymorphinan (compound II of Example 11) and 6 - Phenyloximino-17-methyl-4, 5 α-epoxy-3, 14-dihydroxymorphinan (compound IV of Example IV);

FIG. 11 is a graph illustrating the analgesic effect of 6-Benzyloximino-17-methyl -4,5A-epoxy-3, 14-dihydroxymorphinan (compound III of Example III) on tail flick latency in rats;

FIG. 12 is a graph illustrating the analgesic effect of 6-Phenyloximino-17-methyl -4,5 α-epoxy-3, 14-dihydroxymorphinan (compound IV of Example IV) on tail flick latency in rats;

FIG. 13 is a graph illustrating the analgesic effect of morphine on tail flick latency in rats;

FIG. 14 is a graph illustrating the dose response relationship for the production of increased tail flick latency in rats by the administration of 6-Benzyloximino-17-methyl-4,5 α-epoxy-3, 14-dihydroxymorphinan (compound III of Example III), 6-Phenyloximino-17-methyl-4,5 α-epoxy-3, 14-dihydroxymorphinan (compound IV of Example IV) and morphine;

FIG. 15 is a graph illustrating the analgesic effect of 6-Benzyloximino-17-methyl-4,5 α-epoxy-3, 14-dihydroxymorphinan (compound III of Example III) on tail flick latency in rats;

FIG. 16 is a graph illustrating the analgesic effect of 6-Phenyloximino-17-methyl-4,5 α-epoxy-3, 14-dihydroxymorphinan (compound IV of Example IV) on tail flick latency in rats;

FIG. 18 is a graph illustrating the analgesic effect of 6-Benzyloximino-17-cyclopropylmethyl-4,5 α-epoxy-3, 14 -dihydroxymorphinan (compound XI of Example XI) on morphine - induced analgesia in rats;

FIG. 19 is a graph illustrating the antagonism effect of 6-Phenyloximino-17-cyclopropylmethyl-4,5 α-epoxy-3, 14-dihydroxymorphinan (compound XII of Example XII) of morphine - induced analgesia in rats;

FIG. 21 is a graph illustrating the antagonism effect of 6-Phenyloximino-17-cyclopropylmethyl-4,5 α-epoxy-3, 14-dihydroxymorphinan (compound of XII Example XII) on morphine induced analgesia in rats;

FIG. 23 is a graph illustrating the effect of 6-Phenyloximino-17-cyclopropylmethyl -4,5 α-epoxy-3, 14-dihydroxymorphinan (compound XII of Example XII on the food intake in 24 hour food deprived rats;

FIG. 25 is a graph illustrating the effect of 6-Phenyloximino-17-cyclopropylmethyl 4,5 α-epoxy-3, 14-dihydroxymorphinan (compound XII of Example XII) on the food intake in 24 hour food deprived rats;

FIG. 27 is a graph illustrating the time course of the effects of 6-Phenyloximino-17-cyclopropylmethyl -4,5 α-epoxy-3, 14-dihydroxymorphinan (compound XII of Example XII) on the food intake in 24 hour food deprived rats;

FIG. 28 is a graph illustrating the inability of various doses of 6-Phenyloximino-17-cyclopropylmethyl -4,5 α-epoxy-3, 14-dihydroxymorphinan (compound XII of Example XII) to produce a conditioned taste aversion;

FIG. 29 is a graph illustrating the inability of various doses of 6-Phenyloximino-17-cyclopropylmethyl-4,5 α-epoxy-3, 14-dihydroxymorphinan (compound XII of Example XII) to produce a conditioned taste aversion;

FIG. 31 is a graph illustrating the time course of the antagonism by 6-Phenyloximino-17-cyclopropylmethyl -4,5 α-epoxy-3, 14-dihydroxymorphinan (compound XII of Example XII) of oxymorphonazine (OMZ)-induced analgesia in rats following SC administration;

FIG. 33 is a graph illustrating the time course of the antagonism by 6-Phenyloximinio-17-cyclopropylmethyl -4,5 α-epoxy-3, 14-dihydroxymorphinan (compound XII of Example XII) of OMZ-induced analgesia in rats following PO administration.

DETAILED DESCRIPTION OF THE INVENTION

The structure and formulation of the novel compounds of the invention was based upon the presence of a hydrophobic bonding region in the vicinity of the C-6 position of an opiate agonist or antagonist when complexed with mu-receptor. It is possible this region might be absent or have different dimensions in other opioid receptor types than the mu opioid receptors. The structure of the novel compounds, which contain the hydrophobic bonding region in the vicinity of the C-6 position, provides potent compounds having higher affinity towards a mu-receptor than towards other classes of opioid receptors, rendering them selective. This would therefore permit one to selectively stimulate or antagonize (depending on the compound used) the mu-receptor in tissue also containing other opioid receptors. As a result of the greater affinity and selectivity of the present invention fewer side effects are exhibited by the novel compounds.

Several of the novel compounds suitable for opioid agonists or antagonists have a high affinity and selectivity to displace binding to the kappa or delta subtypes of opioid receptors. This affinity for the kappa or delta receptors is also due to the nature of the C-6 position. As a result of this greater affinity of kappa or delta receptors of the present invention various side effects often times associated with mu agonists or antagonists are avoided.

The high affinity and selectivity of such compounds, e.g.: 6-phenyl or 6-benzyloximino-4, 5 $\alpha$-epoxy-17- cyclopropylmethyl-3, 14-dihydroxymorphinan, has been demonstrated in receptor binding studies and in rats by their ability to provide a long lasting inhibition of morphine-induced analgesia. The analgesic effects of such compounds, e.g.: 6-phenyl or 6-benzyloximino-4,5 $\alpha$-epoxy-17-methyl-3, 14-dihydroxymorphinan, have been demonstrated in rats by utilizing tail flick latencies. The appetite suppression of such compounds, e.g.: 6-phenyl or 6-benzyloximino-4,5 $\alpha$-epoxy-17-cyclopropylmethyl-3, 14dihydroxymorphinan has been demonstrated by a long lasting inhibition of food intake in schedule-adapted food deprived rats.

The novel compounds of the invention can be readily prepared by the reaction of an appropriate ketone, e.g. 7-allyl 4,5 $\alpha$-epoxy-3, 14-dihydroxymorphinan-6-one, with the O-aryl or O-aralkyl hydroxylamines. The aryl or aralkyl may be but is not limited to, for example, phenyl; substituted phenyl wherein the substituent is halogen, hydroxy, nitro, methoxy, methyl, trifluoromethyl, amino, etc.; naphthyl; tetrahydronaphthyl; heterocycle, for example 4- or 5-benzimidazolyl; or, benzyl, substituted benzyl, phenethyl and the like.

The preparation of compounds for administration in pharmaceutical preparations may be in a variety of well known methods known to those skilled in the art of pharmacy. More specifically the novel compounds may be formulated as an acid salt, i.e., HCl salt, sulfate, phosphate, nitrate methanesulfonate, tartrate and other pharmaceutically acceptable salts and compositions.

In parenteral administration of the novel compounds and compositions of the invention may be presented in aqueous injection solutions which may contain antioxidants, buffers, bacteriostats, etc. Extemporaneous injection solutions may be prepared from sterile pills, granules or tablets which may contain diluents, dispersing and surface active agents, binders and lubricants.

In the case of oral administration, fine powders or granules of the compound may be formulated with diluents and dispersing and surface active agents, and may be prepared in a draft in water or in a syrup, in capsules or cachets in the dry state or in a non-aqueous suspension, when a suspending agent may be included.

The compounds may also be administered in tablet form along with optional binders and lubricants, or in a suspension in water or a syrup or an oil or in a water/oil emulsion and may include flavoring, preserving, suspending, thickening and emulsifying agents. The granules or tablets for oral administration may be coated and other pharmaceutically acceptable agents and formulations may be utilized as known to those skilled in the art.

The following examples are illustrative of compounds of the invention but are not to be construed as limiting the invention thereto.

EXAMPLES

Preparation Examples

EXAMPLE I

6-Oximino-17-methyl-4,5 $\alpha$-epoxy-3, 14-dihydroxymorphinan

A solution of oxymorphone (1.2 g, 4 mmol) and hydroxylamine hydrochloride (0.35 g, 5 mmol) in 20 mL of methanol was treated with 2 mL of 10% aqueous NaOH and stirred at room temperature for 15 h. The reaction mixture was poured into water and extracted with 150 mL $CHCl_3$ (3×50 mL). The $CHCl_3$ extract was dried ($MgSO_4$), and evaporated. The residue was recrystallized from THF-petroleum ether yielding 600 mg (47.4%), mp 270-71 C. IR: (KBr): No C=O absorption at 1720 $cm^{-1}$. $^1H$ NMR ($d_6DMSO$) $\delta$ 4.83 (s, $C_5H$), Rf: silica gel EtOAc-EtOH-$NH_4OH$ (100:1:1) 0.18. Anal. Calcd for $C_{17}H_{20}N_2O_4$:C, 64.54; H, 6.37; N, 8.86. Found C, 64.76; H, 6.5; N, 8.58.

EXAMPLE II

6-Methyloximino-17-methyl-4,5 $\alpha$-epoxy-3, 14-dihydroxymorphinan.

A solution of oxymorphone (0.9 g, 3 mmol) and O-methyl hydroxylamine hydrochloride (0.33 g, 3.9 mmol) in 15 mL MeOH containing 1.6 mL of 10% aqueous NaOH was refluxed for 5 h, cooled, diluted with water (approximately 100 mL) and extracted with 150 mL $CHCl_3$ (3×50 mL). The combined extracts were dried ($MgSO_4$), and evaporated. The residue obtained was recrystallized from $CH_2Cl_2$-hexane to yield 0.84 g on the product. It was further purified by flash column chromatography on silica gel, eluting with EtOAc-EtOH-$NH_4OH$ (100:1:1) (approx. size 40 microns). The combined fractions were evaporated in vacuo and the residue obtained was recrystallized from hexane-petroleum ether. Yield: 0.4 g (40%). mp 115-116 C. IR: (KBr): No C=O absorption at 1730 $cm^{-1}$. $^1H$ NMR ($CDCl_3$) $\delta$ 4.92 (s,$C_5H$), 3.85 (s, $OCH_3$) Rf: silica gel 60 in EtOAc-EtOH-$NH_4OH$ (100:1:1) 0.30. Anal. Calcd for: $C_{18} H_{22} N_2O_4$ C, 65.44; H, 6.71; N, 8.48. Found: C, 65.51; H, 6.74; N, 8.46.

EXAMPLE III

6-Benzyloximino-17-methyl-4,5 $\alpha$-epoxy-3, 14-dihydroxymorphinan

Oxymorphone (1.0 g, 3.3 mmol) was dissolved in 20 mL of 95% EtOH containing con-HCl (1 mL). O-Benzylhydroxylamine hydrochloride (0.6 g, 3.75 mmol) was added and the mixture dissolved by warming for a few minutes. Stirring continued for 15 h at room temperature and then the solvent was removed under reduced pressure. The residue was dissolved in water, made alkaline with 5% aqueous $NaHCO_3$ and extracted with 200 mL (4×50 mL) $CHCl_3$. The $CHCl_3$ extract was dried (MgSO$_4$) and evaporated. The residue obtained was chromatographed on silica gel column (approx. size 40 microns) with CHCl$_3$—MeOH (95:5) mixture as eluent. The combined fractions were evaporated in vacuo, the residue dissolved in EtOH, and acidified with conc. HCl. Evaporation of the solvent gave 0.4 g (27%) of the product. mp > 150 C (decomp); IR: (KBr): No absorption for C=O at 1730 cm$^{-1}$; $^1$H NMR (d$_6$DMSO): δ 7.2 (s,C$_6$H$_5$). TLC: Rf: silica gel 60 in CHCl$_3$—MeOH—NH$_4$OH (90:10:1) 0.65. Anal. Calcd for: C$_{24}$H$_{27}$N$_2$ClO$_4$.$\frac{1}{2}$H$_2$O: C, 63.78; H, 6.24; N, 6.20; Cl, 7.84. Found: C, 63.84; H, 6.30; N, 6.17; Cl, 7.83.

EXAMPLE IV

6-Phenyloximino-17-methyl-4,5 α-epoxy-3, 14-dihydroxymorphinan

A mixture of oxymorphone (1 g, 3.3 mmol) and Ophenylhydroxylamine hydrochloride (0.6 g, 4 mmol) in 20 mL of 95% EtOH, was acidified with conc. HCl (1 mL) and stirred for two days. The crystallized product was filtered and collected (1.1 g). The salt was dissolved in water, the solution made alkaline with 5% aqueous NaHCO$_3$ and extracted with 200 mL (4×50 mL) CHCl$_3$. The CHCl$_3$ extract was dried (MgSO$_4$), and evaporated. The residue obtained was chromatographed on a column of silica gel (approx. size 40 microns) with CHCl$_3$—MeOH (94:6). The combined fractions were evaporated in vacuo, the residue dissolved in EtOH, acidified with conc. HCl and concentrated. Dilution with ether precipitated the compound which was filtered and dried. Yield 0.4 g (27%). mp > 140 C (decomp); IR: (KBr): o C=O absorption at 1730 cm$^{-1}$; $^1$H NMR (d$_6$DMSO). 6 7.3 (m,C$_6$H$_5$). Rf: silica gel 60 in CHCl$_3$—MeOH—NH$_{40}$H (90:10:1) 0.75. Anal.Calcd for C$_{23}$H$_{24}$N$_2$O$_4$.HCl.H$_2$O: C, 61.81; H, 6.09; N, 6.27; Cl, 7.93. Found: C, 62.04; H 6.17; N, 6.19; Cl, 7.87.

EXAMPLE V

6-Oximino-17-ally-4,5 α-epoxy-3, 14-dihydroxymorphinan.

A mixture of naloxone hydrochloride (1.085 g, 3 mmol) and hydroxylamine hydrochloride (0.28 g, 4 mmol) was taken up in 30 mL of MeOH containing 2.8 mL of 10% aqueous NaOH. The mixture was stirred at room temperature for 24 h. Water was added (100 mL), and the oxime extracted into CHCl$_3$ (3×50 mL). The extract was dried (MgSO$_4$), and the solvent evaporated. The residue obtained was recrystallized from CH$_2$Cl$_2$-petroleum ether. Yield: 840 mg (81.8%); mp: 119 C. IR: (KBr): No C=O absorption at 1717 cm$^{-1}$. $^1$H NMR (CDCl$_3$) δ 4.98 (s,C$_5$H); Rf: silica gel 60 in EtOAc—EtOH—NH$_4$OH (100:1:1) 0.13. Anal. Calcd for: C$_{19}$H$_{22}$N$_2$O$_4$ C, 66.65; H, 6.48; N, 8.18. Found: C, 66.70; H, 6.52; N, 8.08.

EXAMPLE VI

6-Methyloximino-17-allyl-4,5 α-epoxy-3, 14-dihydroxymorphinan

A solution of naloxone hydrochloride (1.09 g, 3 mmol) and O-methylhydroxylamine hydrochloride (0.33 g, 3.9 mmol) in 15 mL MeOH was stirred overnight. After the addition of 3.2 mL of 10% aqueous NaOH, the mixture was refluxed for 5 h. It was cooled, diluted with approx. 100 mL of water, and extracted with 150 mL CHCl$_3$ (3×50 mL). The combined extracts were dried (MgSO$_4$) and evaporated. The residue obtained was recrystallized from hexane-petroleum ether. Yield 0.8 g, (75%) mp 128°–129° C. IR (KBr): No C=O absorption at 1717 cm$^{-1}$. $^1$H NMR (CDCl$_3$): δ 4.95 (s, C$_5$H), 3.82 (s, OCH$_3$). Rf: silica gel 60 in EtOAc—EtOH—NH$_4$OH (100:1:1) 0.50. Anal. Calcd for C$_{20}$H$_{24}$N$_2$O$_4$ C, 67.40; H, 6.79; N, 7.86. Found: C, 67.27; H, 6.84; N, 7.82.

EXAMPLE VII

6-Benzyloximino-17-allyl-4,5 α-epoxy-3, 14-dihydroxymorphinan

A mixture of naloxone hydrochloride (0.723 g, 2 mmol) and O-benzylhydroxylamine hydrochloride (0.32 g. 2 mmol) in 20 mL of 95% EtOH containing 0.1 mL of conc.HCl was stirred for 15 h at room temperature. The solvent was evaporated under reduced pressure and the residue dissolved in water. The solution was made alkaline with 5% aqueous NaHCO$_3$ and extracted with 100 mL (4×25) of CHCl$_3$. The CHCl$_3$ extract was dried (MgSO$_4$), and evaporated. The residue was chromatographed on a column of silica gel (approx. 40 micron size) with ethyl acetate-toluene mixture (1:1) as eluent. The combined fractions were evaporated in vacuo, the residue dissolved in EtOH, acidified with conc. HCl. and evaporated to dryness. Yield: 0.375 g (40%); mp > 150 C (decomp); IR (KBr): No C=O absorption at 1717 cm$^{-1}$; $^1$H NMR (d$_6$DMSO-D2O): δ 8.00 (s,C$_6$H$_5$). Rf: silica gel 60 in CHCl$_3$—MeOH—NH$_4$OH (90:10:1) 0.65. Anal. Calcd for C$_{26}$H$_9$N$_2$ClO$_4$ C, 66.59; H, 6.23; N, 5.97; Cl, 7.56. Found: C, 66.65; H, 6.43; N, 5.86; Cl, 7.75.

EXAMPLE VIII

6-Phenyloximino-17-allyl-4,5 α-epoxy-3, 14-dihydroxymorphinan

A mixture of naloxone hydrochloride (0.723 g, 2 mmol) and O-phenylhydroxylamine hydrochloride (0.3 g, 2 mmol) was dissolved in 20 mL 95% EtOH, and stirred for 2 days at room temperature. The reaction mixture was poured into 250 mL of ether and the precipitated product was collected by filtration. The compound was dissolved in water, the solution made alkaline with 5% aqueous NaHCO$_3$ and extracted with 150 mL (3×50) of CHCl$_3$. The CHCl$_3$ extract was dried (MgSO$_4$) and evaporated. The residue obtained was chromatographed on a column of silica gel (approx. size 40 microns) with ethyl acetate-toluene mixture (1:1) as eluent. The combined fractions were evaporated in vacuo, the residue dissolved in ethanol, acidified with conc. HCl and concentrated. Addition of ether precipitated the compound, which was collected by filtration and dried (MgSO$_4$). Yield: 0.55 g (60.5%); mp > 180 C (decomp); IR (KBr): No C=O absorption at 1730 cm$^{-1}$. $^1$H NMR (d$_6$DMSO). δ 7.15 (m, C$_6$H$_5$). Rf: silica gel in ethyl acetate - toluene (1:1) 0.42. Anal. Calcd for C$_{25}$H$_{27}$N$_2$ ClO$_4$: C, 66.00; H, 5.98; N, 6.16; Cl, 7.79. Found: C, 65.63; H, 6.03; N, 5.92; Cl, 7.70.

EXAMPLE IX

6-Oximino-17-cycloorooylmethyl-4,5 α-eooxy-3,14-dihydroxymorphinan

A mixture of naltrexone hydrochloride (1.34 g, 3 mmol) and hydroxylamine hydrochloride (0.28 g, 4 mmol) was dissolved in 20 mL of MeOH and 2.8 mL of aqueous NaOH added. The mixture was stirred for 15 h. Water was added (100 mL) and the mixture extracted with 150 mL CHCl$_3$ (3×50 mL). The combined extracts were dried (MgSO$_4$) and evaporated. The residue obtained was chromatographed on a column of silica gel (approx. size 40 microns) using ethyl acetate-ethanol-NH$_4$OH (300:1.5:2) as eluent. The combined fractions were evaporated and the residue recrystallized from CH$_2$Cl$_2$-petroleum ether. Yield: 0.54 g (50.5%) mp 235–236 C. IR (KBr): No C=O absorption at 1720 cm$^{-1}$. $^1$H NMR (CDCl$_3$) δ 6.7 (2d, 2H, J=10 Hz) 5 (s,C$_5$H); Rf: silica gel 60 in ethylacetate-EtOH-NH$_4$OH (100:1:1) 0.22. Anal. Calcd for C$_{20}$H$_{24}$N$_2$O$_4$ C, 67.40; H, 6.79; N, 7.86. Found: C, 67.12; H, 6.88; N, 7.63.

EXAMPLE X

6-Methyloximino-17-cycloorooylmethyl-4,5 α-epoxy-3,14 dihydroxymorphinan

Naltrexone hydrochloride (1.134 g, 3 mmol) was added to a solution of CH$_3$ONH$_2$HCl (0.33 g, 3.9 mmol) in 15 mL MeOH containing 3.2 mL 10% aqueous NaOH. The mixture was refluxed for 5 h, cooled, diluted with approximately 100 mL H$_2$O and extracted with 150 mL CHCl$_3$ (3×50 mL). The combined CHCl$_3$ extracts were dried (MgSO$_4$) and evaporated. TLC showed that the reaction was incomplete and hence the reaction was repeated as before using the mixture, CH$_{30}$NH$_2$HCl (0.165 g, 1.9 mmol) and 0.8 mL of 10% aqueous NaOH. After workup the product was chromatographed on a column of silica gel (approx. size 40 microns) using EtOAC—EtOH—NH$_4$OH (100:1:0.5) as eluent. The fractions were combined, evaporated and the residue recrystallized from hexane-petroleum ether. Yield: 0.55 g (49.6%). mp 172–173 C. IR (KBr): No C=O absorption at 1720 cm$^{-1}$. $^1$H NMR: (CDCl$_3$) δ4.95 (s, C$_5$H), 3.82 (s, OCH$_3$); Rf: silica gel 60 in EtOAc—EtOH—NH$_4$OH (100:1:1) 0.40. Anal. Calcd for C$_{21}$H$_{26}$N$_2$O$_4$ C, 68.09; H, 7.07; N, 7.56. Found: C, 67.96; H, 7.11; N, 7.55.

EXAMPLE XI

6-Benzyloximino-17-cyclopropylmethyl-4,5 α-epoxy-3,14dihydroxymorohinan

A mixture of naltrexone hydrochloride (0.755 g, 2 mmol) and O-benzylhydroxylamine hydrochloride (0.32 g, 2 mmol) in 20 mL of 95% EtOH containing 0.1 mL of conc. HCl was stirred for 15 h. at room temperature. The solvent was evaporated under reduced pressure and the residue dissolved in water. The solution was made alkaline with 5% aqueous NaHCO$_3$. The precipitated product was collected by filtration. The product was purified by chromatography using a silica gel (approx. 40 micron size) column with ethyl acetate-toluene (1:1) mixture as eluent. The combined fractions were evaporated in vacuo, the residue dissolved in EtOH, acidified with conc.HCl and evaporated to dryness. Yield: 0.29 g (30%) mp>200 C (decomp); IR (KBr): No C=O absorption at 1720 cm$^{-1}$. $^1$H NMR (d$_6$DMSO-D$_2$O) δ 7.8 (s, C$_6$H$_5$); Rf: silica gel in ethyl acetate-toluene (1:1) 0.35. Anal. Calcd for: C$_{27}$H$_{31}$N$_2$ClO$_4$ C, 67.14; H, 6.47; N, 5.80; Cl 7.34. Found: C, 66.86; H, 6.44; N, 5.68; Cl, 7.31.

EXAMPLE XII

6-Phenyloximino-17-cyclopropylmethyl-4,5 α-epoxy-3,14-dihydroxymorphinan

A mixture of naltrexone hydrochloride (0.755 g, 2 mmol) and O-phenylhydroxylamine hydrochloride (0.30 g, 2 mmol) was dissolved in 20 mL of 95% EtOH and stirred for 2 days at room temperature. The reaction mixture was poured into 250 mL ether and the precipitated product was collected by filtration. The compound was dissolved in water, the solution made alkaline with 5% NaHCO$_3$, and extracted with 150 mL (3×50 mL) of CHCl$_3$. The CHCl$_3$ extract was dried (MgSO$_4$) and evaporated. The residue obtained was chromatographed on a silica gel (approx. size 40 microns) column with ethyl acetate-toluene (1:1) as eluent. The combined fractions were evaporated in vacuo, the residue dissolved in EtOH, acidified with conc. HCl. and evaporated to dryness. Yield: 0.34 g (36%); mp>150 C (decomp); IR (KBr): No C=O absorption at 1720 cm$^{-1}$ $^1$H NMR (d$_6$DMSO): ε (m, C$_6$H$_5$). Rf: silica gel in ethyl acetate-toluene (1:1) 0.34. Anal. Calcd for C$_{26}$H$_{29}$N$_2$ClO$_4$ C, 66.59; H, 6.23; N, 5.97; Cl, 7.56. Found: C, 66.30; H, 6.21; N, 6.05; Cl, 7.31.

EXAMPLES XIII–XXVII

The following examples were prepared by methods identical to the methods described above for similarly substituted compounds, and are not limitative XIII: 6-[3,4-dimethylphenyl]oximino-17-cyclopropylmethyl-4,5α-epoxy-3,14-dihydroxymorphinan XIV: 6-[1,2,3,4-tetrahydronaphth-1-yl]oximino-17-cyclopropylmethyl-4,5 α-epoxy-3,14-dihydroxymorphinan XV: 6-[2,3-dimethylphenyl]oximino-17-cyclopropylmethyl-4,5 α-epoxy-3,14-dihydroxymorphinan XVI: 6-t-butyloximino-17-cyclopropylethyl-4,5 α-epoxy-3,14-dihydroxymorphinan XVII: 6-[4-trifluoromethylphenyl]oximino-17-cyclopropylmethyl-4,5 α-epoxy-3,14-dihydroxymorphinan XVIII: 6-[4-cyanophenyl]oximino-17-cyclopropylmethyl-4,5α-epoxy-3,14-dihydroxymorphinan XIX: 6-[2-trifluoromethylphenyl]oximino-17-cyclopropylmethyl-4,5 α-epoxy-3,14-dihydroxymorphinan XX: 6-[4-iminoaminomethylphenyl]oximino-17-cyclopropylmethyl-4,5 α-epoxy-3,14-dihydroxymorphinan XXI: 6-[4-phthalimidomethylphenyl]oximino-17-cyclopropylmethyl-4,5 α-epoxy-3,14-dihydroxymorphinan XXII: 6-[2-phenethyl]oximino-17-cyclopropylmethyl-4,5 α-epoxy-3,14-dihydroxymorphinan XXIII: 6-[3-phenylethyl]oximino-17-cyclopropylmethyl-4,5 α-epoxy-3,14-dihydroxymorphinan XXIV: 6-[4-aminomethylphenyl]oximino-17-cyclopropylmethyl-4,5α-epoxy-3,14-dihydroxymorphinan XXV: 6-cyclohexyloximino-17-cyclopropylmethyl-4,5 α-epoxy-3,14-dihydroxymorphinan XXVI: 6-cyclopentyloximino-17-cyclopropylmethyl-4,5 α-epoxy-3,14-dihydroxymorphinan XXVII: 6-[1-adamantyl]oximino-17-cyclopropylmethyl-4,5 α-epoxy-3,14-dihydroxymorphinan

PHARMACOLOGICAL EVALUATION

The analgesic, appetite suppressant and opiate drug abuse treatment properties of the novel compounds were evaluated in vitro and in vivo employing pharmacologically accepted in vitro and in vivo tests as reported in the following Examples XXVIII to XXXII, the accompanying tables and drawings.

EXAMPLE XXVIII

The interaction of some of the novel compounds with mu and delta-type opioid receptors present in brain membranes was examined in vitro. In accordance with the methods of Pert and Snyder (1978), the potency of compounds II–IV, and VI–XII to inhibit specific [$^3$H] DAGO (mu-type receptor) or [$^3$H] DADLE (delta-type receptor) was determined using rat forebrain membranes. Computer assisted analysis (EBDA) was used to determine apparent Ki values for the various compounds. Results are reported in the following Tables 1 and 2.

TABLE 1
POTENCY OF OXYMORPHONE AND ANALOGS TO INHIBIT SPECIFIC BINDING TO MU AND DELTA OPIOID RECEPTORS

| | Ligand | |
|---|---|---|
| COMPOUND | [$^3H$] DAGO Ki (nM) | [$^3$H] DADLE Ki (nM) |
| OXYMORPHONE | 1.6 ± 0.12 (0.77) | 20 ± 8.7 (0.44) |
| OXYMORPHONE-O-METHYLOXIME | 0.97 ± 0.10 (0.91) | 3.44 ± 0.83 (0.56) |
| OXYMORPHONE-O-BENZYLOXIME | 1.58 ± 0.07 (1.06) | 2.80 ± 1.6 (0.70) |
| OXYMORPHONE-O-PHENYLOXIME | *0.84 ± 0.09 (0.74) | 0.91 ± 0.10 (0.72) |

Values represent the MEAN±S.E.M. of the Ki(nM) for each compound to inhibit specific binding of the indicated ligand to rat brain membranes. The values are from two-five separate experiments and were calculated according to the method of Cheng and Prusoff [Biochem. Pharmacol. 1973, 22, 3099–3108] together with the EBDA Program. Numbers in parentheses are the mean Hill coefficients for each compound to inhibit ligand binding.

TABLE 2
POTENCY OF NALTREXONE DERIVATIVES TO INHIBIT SPECIFIC LIGAND BINDING TO MU OR DELTA OPIOID RECEPTORS IN VITRO

| | Ligand | |
|---|---|---|
| COMPOUND | [$^3$H] DAGO Ki (nM) | [$^3$H] DADLE Ki (nM) |
| NALTREXONE | 0.60 ± 0.10 (0.77) | 1.40 ± 1.00 (0.44) |
| NALTREXONE-METHYLOXIME | 0.66 ± 0.06 (0.97) | 1.80 ± 0.22 (0.72) |
| NALTREXONE BENZYLOXIME | 0.55 ± 0.12 (0.97) | 0.70 ± 0.22 (0.85) |
| NALTREXONE OXIME | 0.24 ± 0.03 (0.81) | N.D. |
| NALTREXONE PHENYLOXIME | 0.21 ± 0.08 (0.61) | 1.70 ± 0.51 (0.73) |

Values represent the MEAN±S.E.M. of the Ki(nM) for each compound to inhibit specific binding of the indicated ligand to rat brain membranes. The values are from two÷seven separate experiments and were calculated according to the method of Cheng and Prusoff together with the EBDA program. Numbers in parentheses are the mean Hill coefficients for each compound to inhibit ligand binding. N.D.=not determined Compounds prepared in Examples II–IV and VI–VII (notshown) showed little receptor-type selectivity to displace specifically bound [$^3$H] opiates from opiate receptors. Compounds in Examples IX and XII were 3-fold more potent than the compound in Example X or XI, or naltrexone, to inhibit specific [$^3$H]DAGO binding Furthermore, compound in Example XII was ninefold more selective to inhibit binding at the site labeled by [$^3$H]DAGO than the site labeled [3H]DADLE, whereas naltrexone was only 2.3-fold more selective.

Patterns of inhibition of ligand binding are shown in FIGS. 1–6. FIGS. 1–6 illustrate representative inhibition of specific [$^3$H]DAGO or [3H]DADLE binding to rat brain membranes by analogs of oxymorphone or naltrexone. Compounds prepared in Examples II, III, VIII (not shown), and X displaced [3H] opiate binding as expected (FIGS. 1, 2 and 3). In contrast, compounds XI (FIG. 4), IV, and XII (FIG. 6) appeared to continue to inhibit a percentage of ligand binding at very low drug concentrations.

Compounds as prepared in Examples II, X, IV, IX, XII as well as oxymorphone and naltrexone were examined for their ability to inhibit [3H] opiate binding in a pseudo-irreversible manner (FIG. 7-10). In FIGS. 7–10 the effect of pretreatment of rat forebrain membranes with various compounds on the specific binding of [3H]DAGO or [3H]DADLE is illustrated. Rat forebrain membranes were incubated (30 min; 37°) in the presence of $10^{-8}$M of the indicated drug. Portions of the tissue were washed by centrifugation and resuspension in fresh buffer either 0, 1, 2 or 3 times prior to incubation with the radioligand. Control tissue was treated identically but was not exposed to any drug. The values represent the amount of specific binding observed in membranes following drug pretreatment and the indicated number of washes. The washes themselves did not affect ligand binding. In the FIGS. 7–10 the reported values are the means of three separate experiments. Following incubation (30 min; 37°) of brain membranes in the presence of $10^{-8}$M of the indicated drug, specific [3H]DAGO and [3H]DADLE binding was markedly decreased even after 3 washes of tissue(s), when the tissue had been exposed to compounds of Examples IV or XII. In contrast, binding of the ligand to tissue(s) previously exposed to compounds of Examples II or X did not differ significantly from the tissues exposed to oxymorphone or naltrexone, with complete specific binding being restored after 2–3 washes. The results indicate that compounds of Examples IV and XII, unlike oxymorphone and naltrexone, interact with opiate receptors in vitro in a pseudoirreversible fashion.

EXAMPLE XXVIII

The analgesic properties of the compounds prepared in accordance with Examples III and IV were evaluated in rats using the radiant heat and tail flick paradigm. In the first experiment, rats were injected subcutaneously (S.C.) with one of four doses of the compound of Example III, IV or morphine as a comparison standard immediately following the determination of their baseline flick latencies, and flick latencies were determined at 30 min intervals through 3.5 hr. The doses were 1.11, 2.21, 3.32 or 4.43 μmole/kg for the compound of Example III; 0.56, 1.12, 2.24 or 3.36 μmole/kg for the compound of Example IV; and 3.52, 7.01, 10.5 or 14.0 μmole/kg for morphine. The results for the compounds of Example III, IV and morphine are shown in FIGS. 11, 12, and 13, respectively. Flick latencies in FIGS. 11–13 were determined at 30 minute intervals through 3.5 h and the data was expressed as a percentage of the maximum possible effect (% MPE). A 15 sec. cut-off latency was used to minimize tissue damage. The values shown are the mean values for 6 rats. The oximes are clearly more potent than morphine, with doses of 2.21 μmole/kg of the compound of Example III and 1.12 μmole/kg of the compound of Example IV for producing analgesia approximately equal to that of 10.5 μmole/kg of morphine.

In order to further quantify the differences in analgesic potency, rats were injected S.C. with one of four lower doses of the compounds immediately following the determination of their baseline flick latencies and flick latencies were determined 30 min later. Log dose-response curves for the compounds of Examples III, IV and morphine are shown in FIG. 14. Least squares analyses of these results indicated ED50 values of 0.64, 0.18 and 4.91 μmole/kg for the compounds of Examples III, IV and morphine, respectively. These results indicate that the compounds of Examples III and IV are 4.8- and 17.5-fold, respectively, more potent than morphine as analgesic agents.

Figure 17:
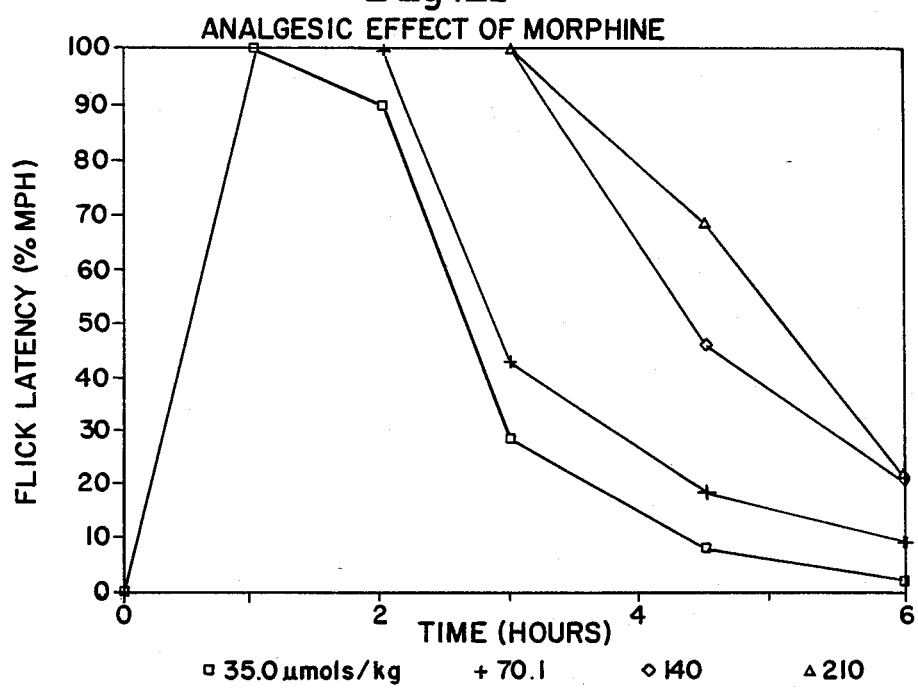

A further investigation was conducted to determine the extent to which compounds of Examples III or IV might produce a more long lasting analgesic effect than morphine at doses higher than those used in the experiment described above. The analgesic effects of doses of morphine and the compound of Example III ranging from approximately 7- to 40-fold higher than their ED50 doses, and doses of the compound of Example IV ranging from approximately 12- to 75-fold higher than its ED50, were determined. Rats were injected S.C. with one of four doses of the compound of Example III, IV or morphine immediately following the determination of their baseline flick latencies and flick latencies were determined at 1, 2, 3, 4.5 and 6 h after drug administration. The doses used were 4.42, 8.85, 17.7 and 26.6 μmole/kg of the compound of Example III; 2.24, 4.48, 8.95 and 13.4 μmole/kg of the compound of Example IV; and 35.0, 70.1, 140 and 210 μmole/kg of morphine. The results for the compounds of Examples III, IV and morphine are shown in FIGS. 15, 16, and 17, respectively in which the data is expressed as a percentage of the maximum possible effect (% MPE). A 15 sec. cut-off latency was used to prevent tissue damage. The values shown are the means of 3-6 rats. As shown in these figures, neither compound, at doses at least as high as 40-times the ED50, produced longer lasting analgesic effects than a comparable, in terms of multiples of the ED50, dose of morphine. None of the morphine treated rats died during the course of the experiment. Out of six rats injected at each dose, the following number of deaths occurred during the experiment after the administration of the indicated compound: for the compound of Example III, 1 died at 8.85, and 3 died at 17.7 and 26.6 μmole/kg; for the compound of Example IV, 1 died at 4.48 and 8.95, and 2 died at 13.4 μmole/kg.

EXAMPLE XXIX

The antagonistic properties of the compounds of Examples XI and XII, i.e. inhibition of morphine-induced analgesia were assessed. Rats were injected IP with the antagonist followed immediately by the subcutaneous (S.C.) administration of 14 μmmol/kg. morphine in a volume of 1 ml/kg saline and tail flick latencies were determined immediately prior to (baseline) as well as 40 minutes after drug administration.

Compounds of Examples XI and XII were injected intraperitoneally (I.P.) in a volume of 4 ml/kg of 0.3% acetic acid. The doses of the compound of Example XI were 1.12, 2.24, 11.19 and 22.37 μmol/kg, and 1.15, 2.31, 11.55 and 23.09 μmol/kg for the compound of Example XII. Tail flick latencies for the two antagonists are shown in FIGS. 18 and 19, and both compounds were able to antagonize the analgesia produced by morphine. In FIGS. 18 and 19 the doses for each group are expressed in μmol/kg. The data represents the mean ±SEM of 3 rats per group. The variability of the response after the two highest doses of the compound of Example XI is due to the small number of animals per group.

Figure 20:
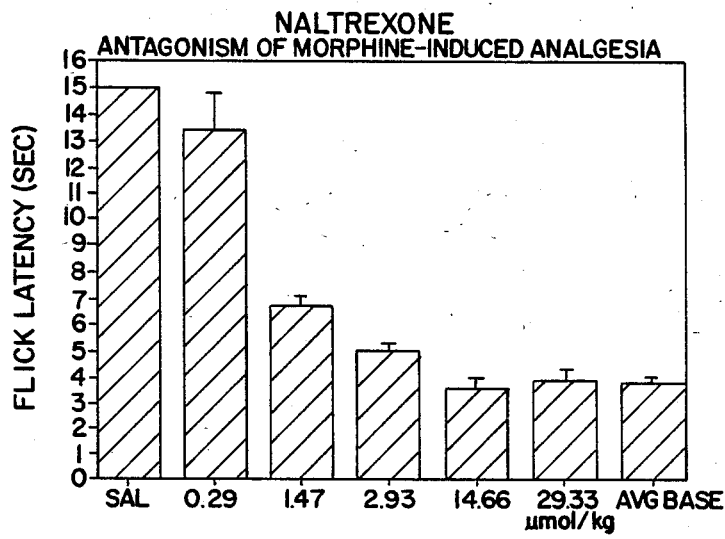

The ability of the compound of Example XII to antagonize morphine-induced analgesia after oral administration was evaluated and compared to that of naltrexone. Testing and drug administration were performed as described above. Naltrexone was administered in doses of 0.19, 1.47, 2.93, 14.66 and 29.33 μmol/kg, and dissolved in 0.9% saline in a volume of 1 ml/kg. The compound of Example XII was given in doses of 0.23, 1.15, 2.31, 11.55 and 23.09 μmol/kg, and dissolved in 0.3% acetic acid in a volume of 4 ml/kg. As illustrated in FIG. 21 the compound of Example XII was able to antagonize the analgesia produced by morphine, although it was less potent than naltrexone (FIG. 20). The data presented in FIGS. 20 and 21 represents the mean ±SEM of 4 rats per group.

EXAMPLE XXX

The appetite suppressing properties of the compound of Example XII were tested and compared to those of naltrexone. Rats were given water and powdered food ad lib for 8 days until food intake had stabilized, and body weight and food and water intakes were recorded at the same time every day. Animals were assigned to treatment groups matched on the basis of their 24 hr food consumption on the last baseline day, and rats were food deprived for 24 hr immediately before injection of the test compound. Naltrexone was administered S.C. at doses of 1.47, 2.93, 14.66 and 29.33 μmol/kg, in a volume of 1 ml/kg of 0.9% saline. The compound of Example XII was injected S.C. at doses of 1.15, 2.31, 11.55 and 23.09 μmol/kg, in a volume of 4 ml/kg of 0.3% acetic acid. Controls were injected with the vehicle solutions in the appropriate volumes. Food and water intakes were measured at 1, 3 and 24 hr after treatment. Data for each measure and time point were analyzed by one-way analysis of variance (ANOVA), and post-hoc comparisons were performed using Dunnett's test in order to compare the control mean to each of the treatment means.

Figure 22:
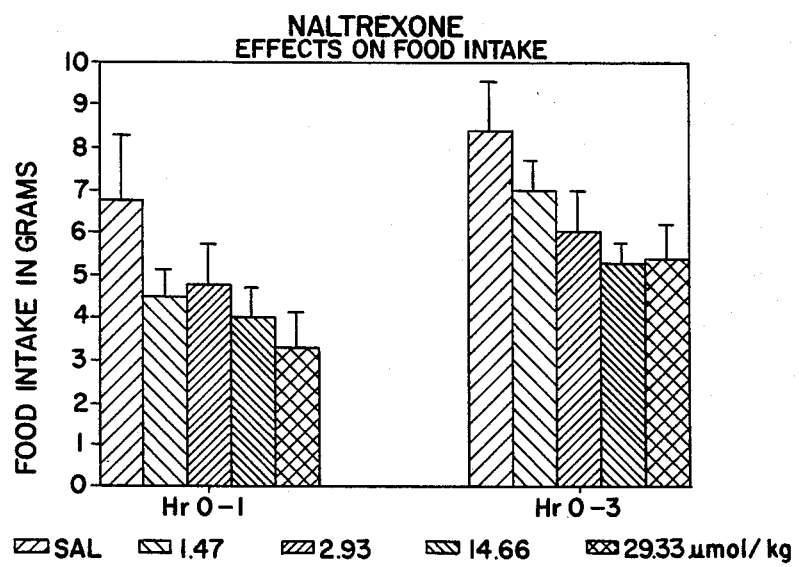

The data for food intake at 1 and 3 hr are presented in FIGS. 22 and 23. For the number of animals per group, see Table 3. The data in FIGS. 22 and 23 represent the means ±SEM for each group. The * represents p>0.05 and **=p<0.001 (Dunnett's test) in FIGS. 22 and 23. ANOVA. indicated a significant effect for naltrexone at 0–3 hr and the compound of Example XII at 0–1 hr. The compound of Example XII at 11.55 and 23.09 μmol/kg significantly inhibited feeding at 1 hr following administration, and the 14.66 and 29.33 μmol/kg doses of naltrexone inhibited feeding at 3 hr following treatment. Feeding had returned to control levels by 24 hr as shown in Table 3 below.

Figure 24:
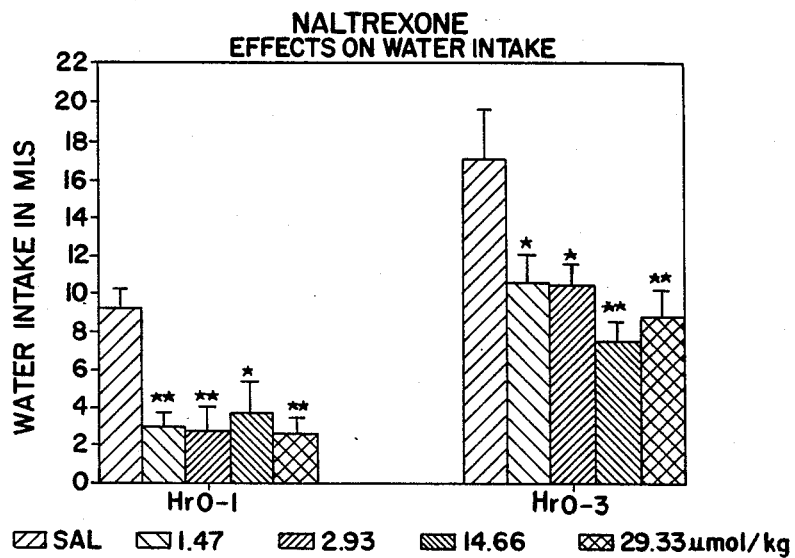

The effects of naltrexone and the compound of Example XII on water intake at 1 and 3 hr are illustrated in FIGS. 24 and 25. The ANOVAs for naltrexone at both 0–1 hr and 0–3 hr were significant. Naltrexone inhibited drinking at all doses tested at the 1 and 3 hr time points. No significant effects were observed for the compound of Example XII at any time point, and for both compounds water intake was equivalent to control levels by 24 hr as indicated in the following Table 3.

TABLE 3

EFFECTS OF NALTREXONE AND EXAMPLE XII ON 24 HR FOOD AND WATER CONSUMPTION IN 24 HR FOOD-DEPRIVED RATS

| Drug/Dose | N | Food Intake in Grams | Water Intake in mL |
|---|---|---|---|
| Saline | 5 | 40.0 ± 5.2 | 70.4 ± 11.3 |
| 0.3% Acetic Acid | 5 | 36.0 ± 3.5 | 72.4 ± 2.8 |
| Naltrexone | | | |
| 1.47 μmol/kg | 4 | 33.0 ± 0.7 | 69.0 ± 3.5 |
| 2.93 μmol/kg | 5 | 33.2 ± 3.0 | 62.4 ± 3.8 |
| 14.66 μmol/kg | 5 | 37.6 ± 4.2 | 53.4 ± 5.5 |
| 29.33 μmol/kg | 3 | 40.7 ± 8.2 | 66.0 ± 2.8 |
| Example XII | | | |
| 1.15 μmol/kg | 6 | 33.3 ± 1.6 | 68.3 ± 8.8 |
| 2.31 μmol/kg | 6 | 31.0 ± 2.0 | 65.0 ± 6.2 |
| 11.55 μmol/kg | 6 | 41.7 ± 7.4 | 60.3 ± 2.1 |
| 23.09 μmol/kg | 5 | 37.6 ± 5.6 | 62.8 ± 3.6 |

Rats were given water and powdered food for 8 days, and following this, animals were food deprived for 24 hr. Immediately prior to the feeding session on the following day, rats were injected S.C. with each compound at the doses indicated below. Data represent the mean ± SEM for each group.

It is evident that the compound of Example XII possesses anorectic activity for 1 hr after administration. Further, the compound of Example XII appears to have negligible effects on water intake, in contrast to naltrexone, which effectively inhibited drinking at all doses tested during the first three hours after administration. This effect may be due to a direct effect of naltrexone on drinking in addition to its effects on food intake, as has been reported previously (see G. A. Olson, R. D. Olson and A.J. Kastin. "Endogenous Opiates 1983:" Peptides 5: 975–992, 1984). The decrease in feeding observed after treatment with naltrexone may be partly attributable to the decreased drinking that also occurs, whereas treatment with the compound of Example XII only affects feeding behavior.

A further experiment evaluated the time course of the anorectic effects of the compound of Example XII in comparison to naltrexone at higher doses. Testing was performed as described above, and baseline measurements were recorded for 7 days. Naltrexone was administered at doses of 14.66, 29.33, 58.65 and 117.30 μmol/kg, in a volume of 1 ml/kg of 0.9% saline. The compound of Example XII was injected at doses of 11.55, 23.09, 46.19 and 92.38 μmol/kg by suspension in a solution of 1:1 DMSO:water in a volume of 3 ml/kg. Food and water intakes were recorded at 1, 2, 4 and 6 h following treatment. The data for food intake are shown in Table 4 as illustrated below.

TABLE 4

TIME COURSE OF THE EFFECTS OF NALTREXONE AND THE COMPOUND OF EXAMPLE XII ON FOOD CONSUMPTION IN 24 HR FOOD-DEPRIVED RATS.

| Drug/Dose | Cumulative Food Intake in Grams | | | |
|---|---|---|---|---|
| | 0–1 Hr | 0–2 Hr | 0–4 Hr | 0–6 Hr |
| Saline | 6.4 ± 0.8 | 6.8 ± 0.9 | 8.8 ± 1.1 | 9.2 ± 1.1 |
| DMSO:H₂O | 5.2 ± 0.9 | 6.8 ± 1.3 | 7.6 ± 0.8 | 8.4 ± 0.5 |
| Naltrexone | | | | |
| 14.66 μmol/kg | 3.6 ± 0.5* | 3.6 ± 0.5* | 4.0 ± 0.0** | 5.2 ± 0.6** |
| 29.33 μmol/kg | 3.2 ± 0.6* | 3.2 ± 0.6** | 4.4 ± 0.5** | 5.2 ± 0.9** |
| 58.65 μmol/kg | 2.8 ± 1.1** | 2.8 ± 1.1** | 3.2 ± 0.9** | 6.4 ± 0.5 |
| 117.30 μmol/kg | 3.6 ± 0.8* | 3.6 ± 0.8* | 4.8 ± 0.9** | 7.6 ± 1.3 |
| Example XII | | | | |
| 11.55 μmol/kg | 2.0 ± 1.0** | 2.0 ± 1.0** | 2.8 ± 0.9** | 3.6 ± 1.3** |
| 23.09 μmol/kg | 2.0 ± 0.7** | 2.4 ± 0.8** | 3.6 ± 1.5** | 3.6 ± 1.5** |
| 46.19 μmol/kg | 2.8 ± 0.6 | 2.8 ± 0.6** | 3.2 ± 0.6** | 3.6 ± 0.8** |
| 92.38 μmol/kg | 3.2 ± 0.6 | 3.2 ± 0.6* | 4.0 ± 0.7* | 4.8 ± 1.1* |

See Table 3 for experimental details, except that baseline measures were recorded for 7 days. Immediately prior to the feeding session on the 8th day, rats were injected S.C. with naltrexone or the compound of Example XII at the doses indicated below. N = 5 per group. Data represent the mean ± SEM. for each group.
* = $p < 0.05$;
** = $p < 0.01$ (Dunnett's test).

ANOVA. indicated significant effects for both naltrexone and the compound of Example XII at all time points. Naltrexone at all doses decreased feeling up to 4 hr after administration, and the two lower doses also decreased feeding at 6 hr post treatment. All doses of the compounds of Example XII significantly decreased feeding from 2 to 6 hr following administration and the two lower doses decreased feeding up to 1 hr following administration.

The data for water intake are illustrated in Table 5 as reported below.

TABLE 5

TIME COURSE OF THE EFFECTS OF NALTREXONE AND THE COMPOUND OF EXAMPLE XII ON WATER CONSUMPTION IN 24 HR FOOD DEPRIVED RATS

| Drug/Dose | Cumulative Water Intake in mL | | | |
|---|---|---|---|---|
| | 0–1 Hr | 0–2 Hr | 0–4 Hr | 0–6 Hr |
| Saline | 9.0 ± 2.4 | 13.5 ± 2.6 | 23.3 ± 2.9 | 25.0 ± 4.3 |
| DMSO:H₂O | 7.0 ± 0.7 | 13.0 ± 1.5 | 18.5 ± 3.8 | 24.3 ± 3.6 |
| Naltrexone | | | | |
| 14.66 μmol/kg | 5.2 ± 1.1 | 9.2 ± 1.1* | 15.2 ± 2.0** | 22.8 ± 2.1 |
| 29.33 μmol/kg | 5.2 ± 0.6 | 8.4 ± 0.5* | 15.2 ± 1.1** | 21.6 ± 3.1 |
| 58.65 μmol/kg | 3.6 ± 0.8** | 6.8 ± 0.6** | 13.2 ± 1.3** | 22.4 ± 2.6 |
| 117.30 μmol/kg | 3.6 ± 0.8** | 9.2 ± 0.9* | 16.0 ± 1.6* | 26.8 ± 3.4 |
| Example XII | | | | |
| 11.55 μmol/kg | 4.8 ± 1.1 | 8.0 ± 1.2* | 15.6 ± 2.5 | 22.0 ± 1.6 |

TABLE 5-continued
TIME COURSE OF THE EFFECTS OF NALTREXONE AND THE COMPOUND OF EXAMPLE XII ON WATER CONSUMPTION IN 24 HR FOOD DEPRIVED RATS

| Drug/Dose | Cumulative Water Intake in mL | | | |
|---|---|---|---|---|
| | 0–1 Hr | 0–2 Hr | 0–4 Hr | 0–6 Hr |
| 23.09 μmol/kg | 4.0 ± 1.0 | 7.2 ± 0.6** | 13.2 ± 2.3 | 19.6 ± 2.2 |
| 46.19 μmol/kg | 5.2 ± 0.9 | 8.0 ± 1.6* | 15.2 ± 1.5 | 20.8 ± 2.9 |
| 92.38 μmol/kg | 4.0 ± 0.7 | 7.6 ± 0.8** | 15.2 ± 1.8 | 21.2 ± 2.1 |

See Table 3 for experimental details, except that baseline measurements were recorded for 7 days. Immediately prior to the feeding session on the 8th day, rats were injected S.C. with naltrexone or the compound of Example XII at the doses indicated. N = 5 per group except Saline and DMSO where N = 4. Data represent the mean SEM for each group.
* = $p < 0.05$;
** = $p < 0.01$ (Dunnett's test).

ANOVA for naltrexone revealed significant effects at 0–1 hr, 0–2 hr and 0–4 hr. The only effect noted for the compound of Example XII occurred at 0–2 hr. As in the previous experiment, the long-lasting effects of naltrexone on water intake were observed, while the effects of the compound of Example XII on drinking were much less apparent.

Figure 26:
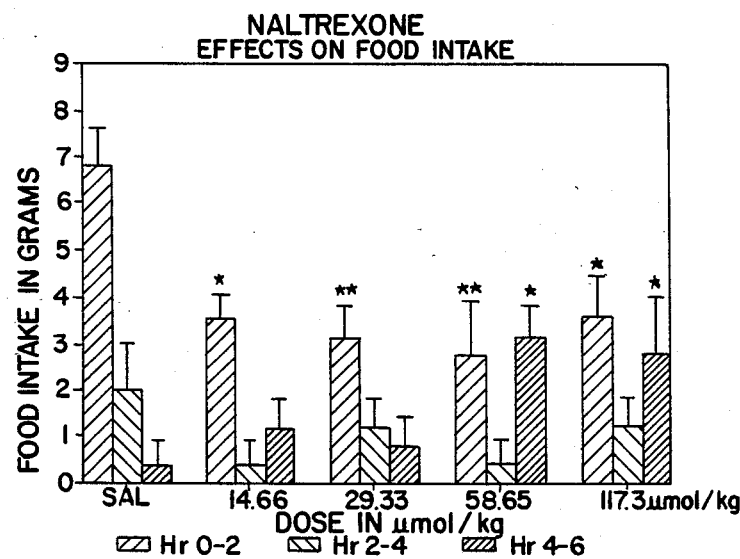

The plotting of data as a function of food intake/2 hr interval instead of cumulative food intake, shows that at the 4–6 hr interval, rats treated with the two highest doses of naltrexone are beginning to resume feeding, while feeding is still suppressed in animals treated with all doses examined of the compound of Example XII (FIGS. 26 and 27). As described above, significant decreases in feeding occur from 0–2 hr following administration of both compounds. Further, ANOVA indicated a significant effect for naltrexone at the 4–6 hr time interval that was due to an increase in food consumption at some doses compared to controls. The food intake of rats treated with the compound of Example XII did not "rebound" at any indicated dose in such a fashion, suggesting that the compound of Example XII at certain doses may have a longer duration of action than naltrexone at similar doses in causing anorexia, demonstrating its superiority as an appetite suppressant.

The ability of a compound to inhibit feeding may not be related to its anorectic properties, but rather to the ability of that compound to produce a conditioned taste aversion. This possibility was tested in the following experiment. Animals were adapted to water deprivation by restricting their access to water to a single 30 min presentation occurring at the same time every day. Baseline water intakes were determined for 7 days until intakes had stabilized, and animals were assigned to treatment groups based on their intakes on the final baseline day. On the following day (day 8), all rats received a bottle of condensed milk (diluted 2:1 water:-milk) in place of the water, and intakes were recorded for 30 min. Fifteen minutes after the milk was removed, rats were administered an I.P. injection of vehicles, LiCl (299.6 μmol/kg) or the compound of Example XII (1.15, 2.31, 11.55 and 23.09 μmol/kg). The compound of Example XII was dissolved in 0.3% acetic acid in a volume of 4 ml/kg. LiCl was dissolved in saline, and serves as a positive control, since it is a compound that reliably produces a strong conditioned taste aversion. This procedure was repeated on day 9. On day 10, all rats were given a two-bottle choice of water or the milk:water solution, and intakes were recorded for 30 min. Data for each experiment were analyzed by one-way ANOVA, and post-hoc comparisons were performed using Dunnett's test.

The effects of the compound of Example XII in producing a conditioned taste aversion are illustrated in FIGS. 28 and 29. In FIGS. 28 and 29 the data represent the mean ±SEM for each group. ** = $p<0.01$ (Dunnett's test). Abbreviations: SAL, saline; AA, 0.3% acetic acid in distilled water; LiCl, lithium chloride. Doses of the compound of Example XII for each group are expressed in μmole/kg. The number of animals per group: SAL, 4; AA, LiCl and each dose of Example XII, 5. FIG. 28: Total milk intake in ml on day 10. FIG. 29: Preference ratio on day 10.

ANOVA indicated a significant effect, but significant decreases in milk intake and in the preference ratio were evident only for LiCl. The compound of Example XII was totally ineffective in producing a conditioned taste aversion at doses that exhibited anorectic properties.

The data confirm that anorectic doses of the compound of Example XII do not exert their effects on food intakes by decreasing water intake or by producing a conditioned taste aversion. This further indicates that this compound does not appear to cause any general malaise at doses up to 23.09 μmol/kg and only affects feeding behavior, further demonstrating its superiority as an appetite suppressant.

EXAMPLE XXXI

The compound of Example XII was evaluated for its potency and duration in the antagonism of oxymorphonazine (OMZ)-induced analgesia. Naltrexone or the compound of Example XII was administered SC or PO immediately followed by SC treatment with 19 μmol/kg of OMZ, and tail flick latencies were determined at 0.5, 1, 1.5, 2, 3, 4, 6 and 8 hr after drug administration. Naltrexone was administered in a volume of 1 ml/kg of distilled H$_2$O, and the compound of Example XII was administered in a volume of 4 ml/kg for SC injections, and 8 ml/kg for PO injections, of 0.3% acetic acid. The doses for SC administration of naltrexone were 0.01, 0.03, 0.13, 0.27 and 1.33 μmol/kg, and 1.33, 2.65, 6.63, 13.26 and 26.53 μmol/kg for oral administration. The doses for SC administration of the compound of Example XII were 0.02, 0.21, 1.07, 2.13 and 10.66 μmol/kg, and 2.13, 5.33, 10.66, 21.32 and 42.64 μmol/kg for PO administration. Data represent the mean SEM of 4–5 animals per group.

Figure 30:
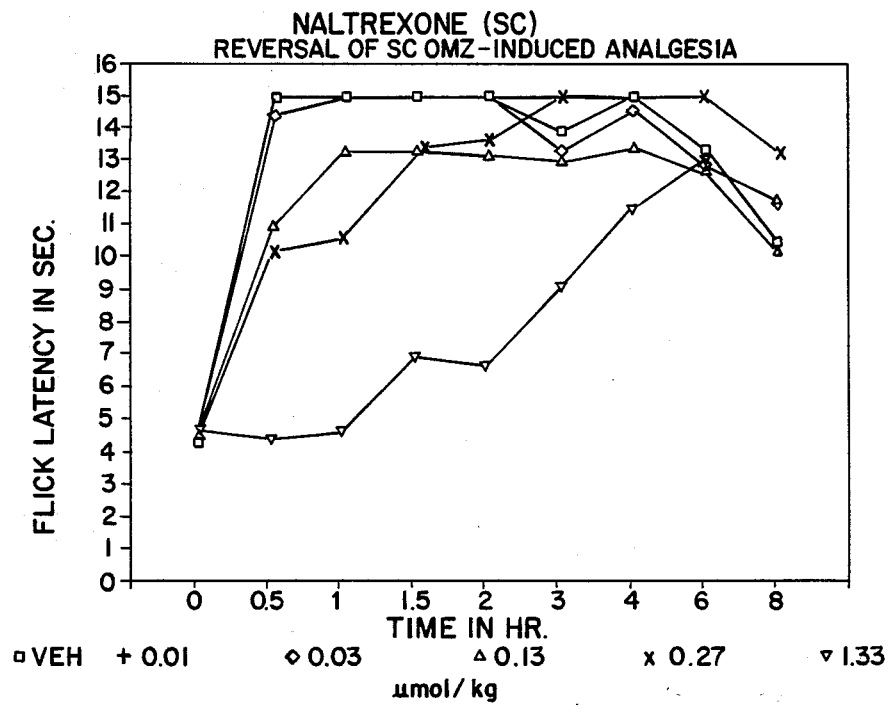
Figure 32:
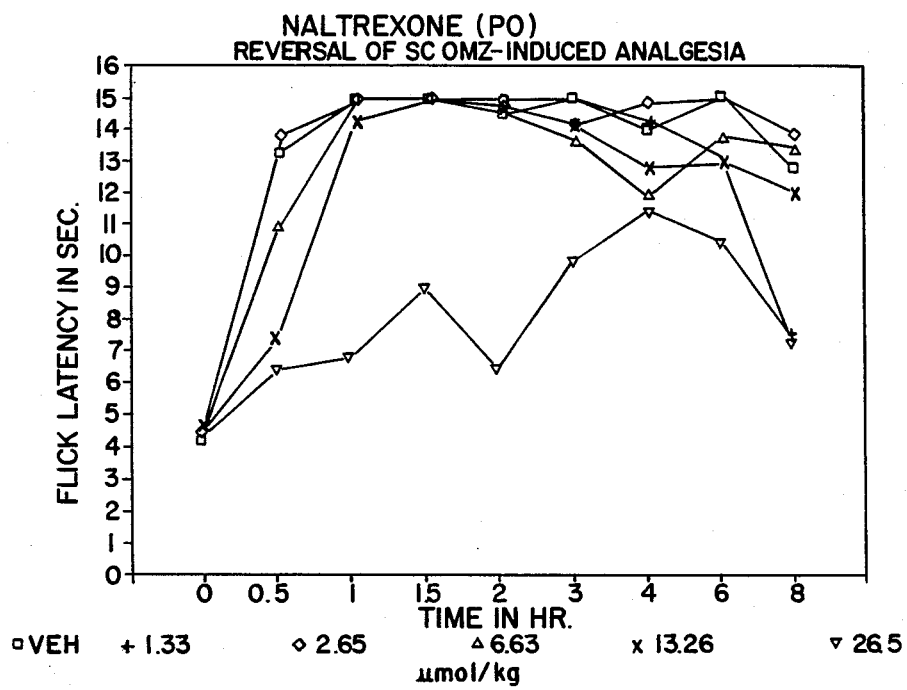

As illustrated in FIG. 30, naltrexone, when SC at a dose of 1.33 μmol/kg, maximally antagonized OMZ-given induced analgesia for up to 1 hr, after which flick latencies began to return to control values. In contrast, SC administration of 10.66 μmol/kg of the compound of Example XII antagonized the analgesia produced by OMZ for the full eight hours of testing (FIG. 31). Lower doses by both routes of administration produced dose-dependent antagonism of the analgesia produced by OMZ. Following PO administration, naltrexone antagonized OMZ induced analgesia for the longest time period at a dose of 26.53 μmol/kg, with a trend for progressive loss of the antagonistic effect over 0.5-4.0 hours, although the reversal was not complete by eight hours (FIG. 32). In contrast, when 42.64 μmol/kg of the compound of Example XII was administered PO, a 50% antagonism of analgesia was observed at 0.5 hours which remained very constant for at least eight hours (FIG. 33).

The above experiments confirm the prolonged duration of action of the compound of Example XII that was suggested by the feeding study data in Example XVI. Although the compound of Example XII was not as potent as naltrexone when administered by the oral route, its longer duration of action in the antagonism of OMZ-induced analgesia as described in Example XXXI, and its ability to inhibit feeding without producing a conditioned taste aversion as described in Example XXX, indicate that the compound of Example XII is a novel and long-lasting opiate antagonist that exhibits superiority as an appetite suppressant.

The interaction of some of the novel compounds with mu, delta and kappa - type opioid receptors present in brain membranes was examined in vitro. In accordance with the methods of Pert and Synder (1978) the potency of compounds XIII to XXVII to inhibit specific [$^3$H] DAGO (mu-type receptor), or [$^3$H] DADLE (Delta-type receptor) using rat forebrain membranes and [$^3$H] EKC (kappa-type receptor) using guiniea pig cerebellum membrane was determined. Computer assisted analysis (EBDA) was used to determine apparent Ki values for the various compounds. The results are reported in Table 6.

TABLE 6
POTENCY OF NALTREXONE DERIVATIVES TO INHIBIT SPECIFIC LIGAND BINDING TO μ, δ OR k OPIATE RECEPTORS IN VITRO

| COMPOUND | Receptor Ligand Source | (Rat Forebrain) (Ki) nM | (Rat Forebrain) (Ki) nM | (GP Cerebellum) (Ki)nM |
|---|---|---|---|---|
| Naltrexone | | 0.60 | 1.40 | 1.81 |
| Nalmefene | | 0.64 | 0.87 | 0.89 |
| Example XI | | 0.55 | 0.87 | |
| Example XII | | 0.30 | 0.58 | 3.47 |
| Example IX | | 0.24 | 1.64 | 2.05 |
| Example XIII | | 1.64 | 2.69 | |
| Example XIV | | 2.76 | 0.60 | 4.66 |
| Example XV | | 1.19 | 1.23 | |
| Example XVI | | 1.01 | 0.41 | 7.39 |
| Example XVII | | 26.4 | 34.4 | |
| Example XCIII | | 2.07 | 1.64 | 12.9 |
| Example XIV | | 3.77 | 1.29 | |
| Example XX | | 0.73 | 1.67 | 0.64 |
| Example XXI | | 7.35 | 2.57 | 18.0 |
| Example XXII | | 0.88 | 0.60 | 0.28 |
| Example XXIII | | 0.32 | 0.44 | 0.01 |
| Example XXIV | | 0.34 | 1.00 | 0.71 |
| Example XXV | | 1.10 | 0.08 | 9.76 |
| Example XXVI | | 0.52 | 0.04 | 7.94 |
| Example XXVII | | 5.39 | 2.63 | 6.41 |

The values represent the MEAN±S.E.M. of the Ki(nM) for each compound to inhibit specific binding of the indicated ligand. Each value represents the mean of three individual experiments performed on separate occasions.

As demonstrated in Table 6 many of compounds showed different receptor type selectivity to displace specifically bound ligands from opiate receptors. For example compounds XXII and XXIII were respectively 3-fold and 100-fold more potent than other compounds or naltrexone to inhibit specific [3H]EKC. This selective potency demonstrates that compounds XXII and XXIII a suitable for binding to Kappa opiate receptors.

Compounds XXV and XXVI on the other hand demonstrate increased potency in selectively displacing specifically bound ligands to [3H] DADLE. These compounds have shown to be respectively 15-fold and 30-fold more potent than Naltrexone at delta receptor.

The analgesic properties of compounds XXII and XXIII were evaluated in rats using the writhing assay and tail flick paradigm. As demonstrated in Table 7 administration of these compounds, like morphine, effectively antagonized the tail-flick response to a heat stimulus in the rat. In addition, both compounds were more potent than morphine to antagonize the writhing response in intraperitoneal injections of acetic acid in the mouse. The writhing assay which uses a chemical stimulus to produce pain, is believed to be more sensitive to kappa agonist activity than other measures of analgesia which uses a heat stimulus (Dykstra, L.A. Behavioral Pharmacology: The Current Status, N.Y.: Allan R. Liss. Inc. 1985). These results further indicate that these two compounds are selective to kappa receptors and possess kappa agonist activity.

TABLE 7
POTENCIES OF VARIOUS OPIOID AGONISTS AND ANTAGONISTS TO PRODUCE ANALGESIA

| Compound | Acetic Acid Induced Writhing in the Mouse | $ED_{50}$ Values (mg/kg) Antagonism of the Tail-Flick Response in the Rat |
|---|---|---|
| Naltrexone | >30 | ND |
| Nalmefene | >30 | ND |
| Morphine | 0.50 | 2.60 |
| Example XXII | 0.01 | 4.02 |
| Example XXIII | 0.02 | 1.84 |

ND = Not determined.

Further assessment of the selectivity of opioid-like compounds demonstrating agonist activity at the kappa receptor sites was carried out using an in vivo assay of the bombesin-induced scratching test. (Cowan A. Trendsin Pharmacology Science, 7:69-72, 1986) With this test the intracerebroventricular administration of bombesin produces a characteristic scratching response. This scratching has been shown to be antagonist in a dose-related fashion. Opioid agonists which are nonselective as well as those agonists with selectivity for the mu or delta type receptors are generally inactive in this type of bioassay. Using this bombesin-induced scratching test 6[3-phenylpropyl] oximino naltrexone produced a mean A₅₀ value of 0.08 mg/kg following subcutaneous administration. The analgesic properties of the novel compounds were also evaluated by tail-flick latencies, as shown in Table 8, taken at 30 minute and 1 hour intervals up to 8 hours where the data is expressed at the percent antagonism. The data demonstrates the potency of the novel compounds is greater than naltrexone.

TABLE 8

Oxymorphonazine Antagonism (S.C.) Duration of Action

| Compound | ED 50(mg/kg) | ED 100 | Dose Tested (mg/kg) | Percent Antagonism at Various Times After ED 100 | | | | | | |
|---|---|---|---|---|---|---|---|---|---|---|
| | | | | 1 Hr | 1.5 Hr | 2 Hr | 3 Hr | 4 Hr | 6 Hr | 8 Hr |
| Naltrexone | 0.07 | 0.62 | 0.5 | 98 | 76 | 79 | 47 | 30 | 4 | 4 |
| Nalmefene | 0.12 | 1.35 | 1.0 | 85 | 92 | 83 | 73 | 46 | 0 | 37 |
| Example XI | 1.20 | 12.98 | 10.0 | 72 | 86 | 91 | 93 | 103 | 122 | 64 |
| Example XII | 0.34 | 3.10 | 2.5 | 90 | 92 | 91 | 77 | 91 | 92 | 80 |
| Example XIII | 0.09 | 0.74 | 0.5 | 77 | 72 | 67 | 79 | 72 | 71 | 97 |
| Example XIV | 0.02 | 6.73 | 5.0 | 80 | 84 | 82 | 84 | 83 | 41 | 20 |

This data as set forth above further demonstrates that compounds XXV and XXVI naltrexone possess selectivity for the delta type receptors. These compounds which possess delta selectivity for opioid receptor with antagonist properties are useful for the treatment of endotoxic shock or stimulation of immune system when introduced in an effective amount with a suitable pharmaceutical carrier.

Pharmaceutical compositions have been prepared containing a mixture of opioid agonists and antagonists which have been beneficial in the reversal of hypovolemic shock in animals. The novel compounds can be incorporated into pharmaceutical compounds as a mixture of kappa agonists and delta antagonists. This novel mixture is particularly suitable for the treatment of shock or immune deficiency since the delta receptor antagonist is beneficial in treating shock or immune deficiency and reversing the associated cardiovascular responses while the kappa receptor agonist permits the alleviation of pain and is able to circumvent the respiratory depression associated with the use of mu agonists.

The pharmaceutical composition is prepared according to standard methods using a suitable pharmaceutical carrier. The amount introduced is dependent on the type of treatment and potency of the agonist or antagonist used. Similarly, the proportions of the agonist are also determined by the type of treatment and the potency of each compound.

While the invention has been described in terms of various preferred embodiments, the skilled artisan will appreciate that various modifications, substitutions, omissions and excipients may be made without departing from the spirit of the invention or the scope of the appended claims.

What is claimed is:

1. A potent, selective opioid kappa receptor agonist or a delta or mu antagonist compound of the formula:

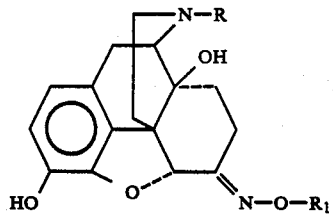

wherein R is cyclopropylmethyl and R₁ is selected from the group consisting of phenylethyl, naphthyl, tetrahydronaphthyl, phenylpropyl, cyclohexyl, cyclopentyl, iminoaminomethylphenyl, dimethylphenyl, t-butyl, trifluormethylphenyl, cyanophenyl, 4-benzimidazolyl, 5-benzimidazolyl, or

wherein R₂ is selected from the group consisting of hydrogen, halogen, hydroxy, nitro, methoxy, methyl, trifluormethyl or amino and the pharmaceutically acceptable salts thereof.

2. The potent, selective opioid kappa receptor agonist compound according to claim 1 that is 6-(2-phenylethyl)oximino-17-cyclopropylmethyl-4,5 α-epoxy-3,14-dihydroxymorphinan.

3. The potent, selective opioid kappa receptor agonist compound according to claim 1 that is 6-(3-phenylpropyl)oximino-17-cyclopropylmethyl-4,5 α-epoxy-3,14-dihydroxymorphinan.

4. A pharmaceutial composition for relieving pain which comprises a pain relieving effective amount of one or more compounds of claim 1 with a pharmaceutically acceptable carrier and/or diluent.

5. A process of relieving pain in an animal in need thereof which comprises administering said compound of claim 1 or 15 parenterally, nasally, orally, rectally or a combination thereof to said animal in need thereof.

6. A pharmaceutical composition for treating opiate drug abuse which comprises an effective amount of one or more compounds of claim 1 with a pharmaceutically acceptable carrier and/or diluent.

7. A process for treating opiate drug abuse in an animal in need thereof which comprises administering said compound of claims 1 or 6 parenterally, orally, nasally, rectally or a combination thereof to said animal in need thereof.

8. The potent, kappa selective opioid receptor agonist compound of the formula:

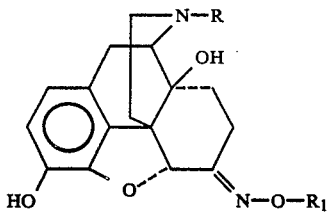

wherein R is cyclopropylmethyl and wherein $R_1$ is 2-phenylethyl or 3-phenylpropyl and the pharmaceutically acceptable salts thereof.

9. A pharmaceutical composition for relieving pain comprising an effective amount of one or more of the kappa selective opioid receptor agonist compounds of claim 8 with a pharmaceutically acceptable carrier and/or diluent.

10. A process for relieving pain in an animal comprising administering an effective amount of the composition of claim 9 parenterally, orally, nasally, rectally or a combination thereof to said animal in need thereof.

11. A potent, delta selective opioid receptor antagonist compound having the formula:

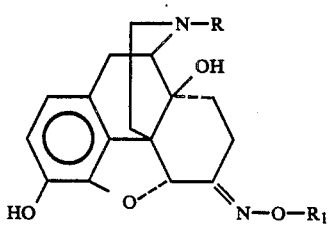

wherein R is cyclopropylmethyl and $R_1$ is t-butyl, cyclohexyl or cyclopentyl and the pharmaceutically acceptable salts thereof.

12. The potent, delta selective opioid receptor antagonist of claim 11 that is 6-cyclohexyloximino-17-cyclopropylmethyl-4,5 α-epoxy-3,14 dihydroxy-morphinan.

13. The potent, delta selective opioid receptor antagonist of claim 11 that is 6-cyclopentyloximino-17-cyclopropylmethyl-4,5 α-epoxy-3, 14-dihydroxymorphinan.

14. A pharmaceutical composition for treating shock or immune deficiency comprising an effective amount of one or more compounds of claim 11 with a pharmaceutically acceptable carrier and/or diluent.

15. A process of treating shock or immune deficiency in an animal in need thereof which comprises administering said composition of claim 14 parenterally, nasally, orally, rectally or a combination thereof to said animal in need thereof.

16. The potent, delta selective opioid receptor antagonist of claim 11 that is 6-t-butyloximino-17-cyclopropylmethyl-4,5 α-epoxy-3,14-dihydroxymorphinan.

17. A pharmaceutical composition for relieving pain which comprises a pain relieving effective amount of one or more compounds of claim 11 with a pharmaceutically acceptable carrier and/or diluent.

18. A process of relieving pain in an animal in need thereof which comprises administering said compound of claim 11 or 17 parenterally, nasally, orally, rectally or a combination thereof to said animal in need thereof.

19. A pharmaceutical composition for treating opiate drug abuse which comprises an effective amount of one or more compounds of claim 11 with a pharmaceutically acceptable carrier and/or diluent.

20. A process for treating opiate drug abuse in an animal in need thereof which comprises administering said compound of claims 11 or 19 parenterally, orally, nasally, rectally or a combination thereof to said animal in need thereof.

21. A pharmaceutical composition for suppressing appetite which comprises an effective amount of one or more compounds of claim 11 with a pharmaceutically acceptable carrier and/or diluent.

22. A process for suppressing appetite in an animal in need thereof which comprises administering said compound of claims 11 or 21 parenterally, orally, nasally, rectally or a combination thereof to said animal in need thereof.

* * * * *